US006274139B1

(12) United States Patent
Gwynn et al.

(10) Patent No.: US 6,274,139 B1
(45) Date of Patent: Aug. 14, 2001

(54) TOPOISOMERASE I

(75) Inventors: Michael N. Gwynn, Chester Springs; Howard Kallendar, King of Prussia; Leslie M. Palmer, Malvern, all of PA (US)

(73) Assignees: SmithKline Beecham Corporation, Philadelphia, PA (US); SmithKline Beecham p.l.c. (GB)

( * ) Notice: Subject to any disclaimer, the term of this patent is extended or adjusted under 35 U.S.C. 154(b) by 0 days.

(21) Appl. No.: 09/340,479

(22) Filed: Jun. 30, 1999

Related U.S. Application Data

(62) Division of application No. 08/946,475, filed on Oct. 7, 1997, now Pat. No. 6,013,505.
(60) Provisional application No. 60/027,973, filed on Oct. 8, 1996.

(51) Int. Cl.$^7$ .......................... A61K 38/51; A61K 38/00; C12Q 1/58; C12N 9/90

(52) U.S. Cl. ........................... 424/94.5; 435/12; 435/183; 435/196; 435/233; 514/12; 530/324

(58) Field of Search .......................... 424/94.5; 435/233, 435/183, 196; 514/12; 530/324

(56) References Cited

U.S. PATENT DOCUMENTS

| 5,004,758 | 4/1991 | Boehm et al. ........................ 514/283 |
| 6,013,505 | * 1/2000 | Gwynn et al. ....................... 435/233 |

FOREIGN PATENT DOCUMENTS

| 0 786 519 | 7/1997 | (EP) . |
| 0 837 138 | 4/1998 | (EP) . |
| WO 97/30070 A | 8/1997 | (WO) . |

OTHER PUBLICATIONS

Lerner, et al: "High Throughput Screen for Inhibitors of Bacterial DNA Topoisomerase I Using the Scintillation Proximity Assay" *Journal of Biomolecular Screening*, vol. 1, No. 3; pp. 135–143 (1996).
Snewin, et al.: "Cloning and Characterisation of a gene from *Plasmodium vivax* and *P. knowlesi*: homology with valine–tRNA snythetase" *Gene* vol. 173 No. 2 (1996) pp. 137–145.
Brown, et al: "A Sign Inversion Mechanism for Enzymatic Supercoiling of DNA" *Science* vol. 206, pp. 1081–1083 (1979).
Yoshimora, et al: "*Bacillus subtilis* secretes a foreign protein by the signal sequence of *Bacillus amyloliquefaciens* neutral protease" *Appl. Microbiol* vol. 23, pp. 250–256 (1986).
Huang, et al: "DNA Topology and Its Biological Effects" *ColdSpring Harbor Laboratory Press* (1990), pp. 265–284.
Kato, et al.: "Purification and Characterization of DNA Topoisomerase IV in *Escherichia coli*" *Journal of Biological Chemistry* vol. 267, No. 3, pp. 25676–25684 (1992).
Hsieh, et al: "Mechanistic Aspects of Type–II DNA Topoisomerase" *ColdSpring Harbor Laboratory Press* (1990), pp. 243–263.
Kim, et al.: "Identification of the Yeast TOP3 Gene Products as a Single Strand–specific DNA Topoisomerase" *Journal of Biological Chemistry*, vol. 267, No. 24, pp. 17178–17185 (1992).
Hanai, et al.: "Human TOP3: A single–copy gene encoding DNA topoisomerase III" *Proc. Natl. Acad. Sci. USA* vol. 93, pp. 3653–3657 (1996).
Siedlecki, et al.: "Characterization of a prokaryotic topoisomerase I activity in chloroplast extracts from spinach" *Nucleic Acids Research* vol. 11, pp. 1523–1536. (1983).
Kikuchi, et al: "DNA Topology and Its Biological Effects" *ColdSpring Harbor Laboratory Press* (1990), pp. 285–298.
De La Tour, et al.: "Reverse Gyrase in Thermophilic Eubacteria" *Journal of Bacteriology* vol. 173, No. 12, pp. 3921–3923 (1991).
Slesarev, et al.: "DNA Topoisomerse III from Extremely Thermophilic Archaebacteria" *Journal of Biological Chemistry* vol.266, No. 19, pp. 12321–12328 (1991).
Neil Osheroff: "Biochemical Basis for the Interactions of Type I and Type II Topoisomerases with DNA" *Pharmac. Ther*. vol. 41, pp. 223–241 (1989).
Karl Drlica: "Biology of Bacterial Deoxyribonucleic Acid Topoisomerase" *Microbiological Reviews* vol. 48, No. 4, pp. 273–289 (1984).
Glisson, et al: "DNA Topoisomerase II: A Primer on the Enzyme and its Unique Role as a Multidrug Target in Cancer Chemotherapy" *Pharmac. Ther*. vol. 332, pp. 89–106 (1987).
Bodley, et al.: "Topoisomerases as Novel Targets for Cancer Chemotherapy" *Bio/technology* vol. 6 pp. 1315–1319 (1988).
Leroy F. Liu: "DNA Topoisomerase Poisons as Antitumor Drugs" *Annu. Rev. Biochem*. vol. 58, pp. 351–375. (1989).
Amy Luttinger: "The Twisted 'life' of DNA in the Cell: bacterial topoisomerases" *Molecular Microbiology* vol. 15(4), pp. 601–606 (1995).

(List continued on next page.)

*Primary Examiner*—Einar Stole
(74) *Attorney, Agent, or Firm*—Edward R. Gimmi; Thomas S. Deibert; William T. King

(57) ABSTRACT

Topoisomerase I polypeptides and DNA and RNA encoding such Topoisomerase I polypeptides and a procedure for producing such polypeptides by recombinant techniques is disclosed. Also disclosed are methods for utilizing such Topoisomerase I for the treatment of infection, particularly bacterial infections. Antagonists against such Topoisomerase I and their use as a therapeutic to treat infections, particularly bacterial infections are also disclosed. Also disclosed are diagnostic assays for detecting diseases related to the presence of Topoisomerase I nucleic acid sequences and the polypeptides in a host. Also disclosed are diagnostic assays for detecting polynucleotides encoding Staphylococcal Topoisomerase I and for detecting the polypeptide in a host.

17 Claims, 12 Drawing Sheets

OTHER PUBLICATIONS

Berlani, et al.: "Transfer RNA genes in the cap–oxi1 region of yeast mitochondrial DNA" *Nucleic Acids Research* vol. 8, No. 21 (1980).

Joaquim Roca: "The mechanisms of DNA topoisomerases" *TIBS* vol. 20, pp. 156–160 (1995).

S. De. Jong: "Cloning and Sequencing of the Top1 Gene, the Gene Encoding B. Subtilis DNA Topoisomerase I" *EMBL Database entry BSSMF*, Accession No. L27797, Aug. 11, 1994.

* cited by examiner

FIGURE 1. Topoisomerase I cDNA Sequence (SEQ ID NO: 1)

```
ATAACGAGTT GCTTCATATT TCTTTTGTTA CCCTTTGTAA TTTATTTTTT AATAAAATCT    60
ATAAAAAATA GACAGGGAAA ATGATTTGTT TAGATATAAA ACGTTGACAA AAGCAAAATT   120
AAGCGTTTAT CATTTATCTT TAGTAATTAG ATTAGCGAGG GGGAA ATG ACA TTG GCA   177
                                                 Met Thr Leu Ala
                                                  1
```

| GAT | AAT | TTA | GTC | ATT | GTT | GAA | TCG | CCT | GCA | AAA | GCA | AAA | ACC | ATT | GAA | 225 |
|---|---|---|---|---|---|---|---|---|---|---|---|---|---|---|---|---|
| Asp | Asn | Leu | Val | Ile | Val | Glu | Ser | Pro | Ala | Lys | Ala | Lys | Thr | Ile | Glu | |
| 5 | | | | 10 | | | | | 15 | | | | | 20 | | |

| AAG | TAT | TTA | GGT | AAG | AAA | TAT | AAA | GTT | ATA | GCT | TCA | ATG | GGA | CAC | GTC | 273 |
|---|---|---|---|---|---|---|---|---|---|---|---|---|---|---|---|---|
| Lys | Tyr | Leu | Gly | Lys | Lys | Tyr | Lys | Val | Ile | Ala | Ser | Met | Gly | His | Val | |
| | | | | 25 | | | | | 30 | | | | | 35 | | |

| AGA | GAC | TTA | CCA | AGA | AGT | CAA | ATG | GGT | GTC | GAC | ACT | GAA | GAT | AAT | TAC | 321 |
|---|---|---|---|---|---|---|---|---|---|---|---|---|---|---|---|---|
| Arg | Asp | Leu | Pro | Arg | Ser | Gln | Met | Gly | Val | Asp | Thr | Glu | Asp | Asn | Tyr | |
| | | | 40 | | | | | 45 | | | | | 50 | | | |

| GAA | CCA | AAA | TAT | ATA | ACA | ATA | CGC | GGA | AAA | GGT | CCT | GTT | GTA | AAA | GAA | 369 |
|---|---|---|---|---|---|---|---|---|---|---|---|---|---|---|---|---|
| Glu | Pro | Lys | Tyr | Ile | Thr | Ile | Arg | Gly | Lys | Gly | Pro | Val | Val | Lys | Glu | |
| | | 55 | | | | | 60 | | | | | 65 | | | | |

| TTG | AAA | AAA | CAT | GCA | AAA | AAA | GCG | AAA | AAC | GTC | TTT | CTC | GCA | AGT | GAC | 417 |
|---|---|---|---|---|---|---|---|---|---|---|---|---|---|---|---|---|
| Leu | Lys | Lys | His | Ala | Lys | Lys | Ala | Lys | Asn | Val | Phe | Leu | Ala | Ser | Asp | |
| | 70 | | | | | 75 | | | | | 80 | | | | | |

| CCC | GAC | CGT | GAA | GGT | GAA | GCA | ATT | GCT | TGG | CAT | TTA | TCA | AAA | ATT | TTA | 465 |
|---|---|---|---|---|---|---|---|---|---|---|---|---|---|---|---|---|
| Pro | Asp | Arg | Glu | Gly | Glu | Ala | Ile | Ala | Trp | His | Leu | Ser | Lys | Ile | Leu | |
| 85 | | | | 90 | | | | | 95 | | | | | 100 | | |

| GAG | CTT | GAA | GAT | TCT | AAA | GAA | AAT | CGC | GTT | GTT | TTC | AAC | GAA | ATA | ACT | 513 |
|---|---|---|---|---|---|---|---|---|---|---|---|---|---|---|---|---|
| Glu | Leu | Glu | Asp | Ser | Lys | Glu | Asn | Arg | Val | Val | Phe | Asn | Glu | Ile | Thr | |
| | | | | 105 | | | | | 110 | | | | | 115 | | |

| AAA | GAC | GCT | GTT | AAA | GAA | AGT | TTT | AAA | AAT | CCT | AGA | GAA | ATT | GAA | ATG | 561 |
|---|---|---|---|---|---|---|---|---|---|---|---|---|---|---|---|---|
| Lys | Asp | Ala | Val | Lys | Glu | Ser | Phe | Lys | Asn | Pro | Arg | Glu | Ile | Glu | Met | |
| | | | 120 | | | | | 125 | | | | | 130 | | | |

FIGURE 1A

| | | | | | | | | | | | | | | | |
|---|---|---|---|---|---|---|---|---|---|---|---|---|---|---|---|
| AAC | TTA | GTC | GAT | GCA | CAA | CAA | GCG | CGT | CGA | ATA | TTA | GAT | AGA | TTG | GTT | 609 |
| Asn | Leu | Val | Asp | Ala | Gln | Gln | Ala | Arg | Arg | Ile | Leu | Asp | Arg | Leu | Val | |
| | | 135 | | | | 140 | | | | | 145 | | | | | |

| GGC | TAT | AAC | ATC | TCG | CCA | GTT | CTA | TGG | AAA | AAA | GTG | AAA | AAA | GGT | TTG | 657 |
| Gly | Tyr | Asn | Ile | Ser | Pro | Val | Leu | Trp | Lys | Lys | Val | Lys | Lys | Gly | Leu | |
| | | 150 | | | | 155 | | | | 160 | | | | | | |

| TCA | GCG | GGT | CGA | GTT | CAA | TCT | GTT | GCA | CTT | CGT | TTA | GTC | ATT | GAC | CGT | 705 |
| Ser | Ala | Gly | Arg | Val | Gln | Ser | Val | Ala | Leu | Arg | Leu | Val | Ile | Asp | Arg | |
| 165 | | | | 170 | | | | 175 | | | | 180 | | | | |

| GAA | AAT | GAA | ATT | CGA | AAC | TTT | AAA | CCA | GAA | GAA | TAT | TGG | ACT | ATT | GAA | 753 |
| Glu | Asn | Glu | Ile | Arg | Asn | Phe | Lys | Pro | Glu | Glu | Tyr | Trp | Thr | Ile | Glu | |
| | | | | 185 | | | | 190 | | | | 195 | | | | |

| GGA | GAA | TTT | AGA | TAC | AAA | AAA | TCA | AAA | TTC | AAT | GCT | AAA | TTC | CTT | CAT | 801 |
| Gly | Glu | Phe | Arg | Tyr | Lys | Lys | Ser | Lys | Phe | Asn | Ala | Lys | Phe | Leu | His | |
| | | | 200 | | | | 205 | | | | 210 | | | | | |

| TAT | AAA | AAT | AAA | CCT | TTT | AAA | TTA | AAA | ACG | AAA | AAA | GAT | GTT | GAG | AAA | 849 |
| Tyr | Lys | Asn | Lys | Pro | Phe | Lys | Leu | Lys | Thr | Lys | Lys | Asp | Val | Glu | Lys | |
| | | 215 | | | | 220 | | | | 225 | | | | | | |

| ATT | ACA | GCT | GCA | CTA | GAT | GGA | GAT | CAA | TTC | GAA | ATT | ACA | AAC | GTG | ACT | 897 |
| Ile | Thr | Ala | Ala | Leu | Asp | Gly | Asp | Gln | Phe | Glu | Ile | Thr | Asn | Val | Thr | |
| | | 230 | | | | 235 | | | | 240 | | | | | | |

| AAA | AAA | GAA | AAA | ACG | CGT | AAT | CCA | GCA | AAC | CCA | TTT | ACA | ACT | TCT | ACA | 945 |
| Lys | Lys | Glu | Lys | Thr | Arg | Asn | Pro | Ala | Asn | Pro | Phe | Thr | Thr | Ser | Thr | |
| 245 | | | | 250 | | | | 255 | | | | 260 | | | | |

| TTA | CAA | CAA | GAG | GCG | GCA | CGT | AAA | TTA | AAC | TTT | AAA | GCA | AGA | AAA | ACA | 993 |
| Leu | Gln | Gln | Glu | Ala | Ala | Arg | Lys | Leu | Asn | Phe | Lys | Ala | Arg | Lys | Thr | |
| | | | | 265 | | | | 270 | | | | 275 | | | | |

| ATG | ATG | GTC | GCA | CAA | CAA | TTA | TAT | GAA | GGT | ATA | GAT | TTG | AAA | AAA | CAA | 1041 |
| Met | Met | Val | Ala | Gln | Gln | Leu | Tyr | Glu | Gly | Ile | Asp | Leu | Lys | Lys | Gln | |
| | | | | 280 | | | | 285 | | | | 290 | | | | |

FIGURE 1B

```
GGT ACG ATT GGT TTA ATA ACA TAT ATG AGA ACC GAT TCT ACA CGT ATT     1089
Gly Thr Ile Gly Leu Ile Thr Tyr Met Arg Thr Asp Ser Thr Arg Ile
         295                 300                 305

TCA GAT ACT GCC AAA GCT GAA GCA AAA CAG TAT ATA ACT GAT AAA TAC     1137
Ser Asp Thr Ala Lys Ala Glu Ala Lys Gln Tyr Ile Thr Asp Lys Tyr
     310                 315                 320

GGT GAA TCT TAC ACT TCT AAA CGT AAA GCA TCA GGG AAA CAA GGT GAC     1185
Gly Glu Ser Tyr Thr Ser Lys Arg Lys Ala Ser Gly Lys Gln Gly Asp
325                 330                 335                 340

CAA GAT GCC CAT GAG GCT ATT AGA CCT TCA AGT ACT ATG CGT ACG CCA     1233
Gln Asp Ala His Glu Ala Ile Arg Pro Ser Ser Thr Met Arg Thr Pro
             345                 350                 355

GAT GAT ATG AAG TCA TTT TTG ACG AAA GAC CAA TAC CGA TTA TAC AAA     1281
Asp Asp Met Lys Ser Phe Leu Thr Lys Asp Gln Tyr Arg Leu Tyr Lys
         360                 365                 370

TTA ATT TGG GAA CGA TTT GTT GCT AGT CAA ATG GCT CCA GCA ATA CTT     1329
Leu Ile Trp Glu Arg Phe Val Ala Ser Gln Met Ala Pro Ala Ile Leu
     375                 380                 385

GAT ACA GTC TCA TTA GAC ATA ACA CAA GGT GAC ATT AAA TTT AGA GCG     1377
Asp Thr Val Ser Leu Asp Ile Thr Gln Gly Asp Ile Lys Phe Arg Ala
         390                 395                 400

AAT GGT CAA ACA ATC AAG TTT AAA GGA TTT ATG ACA CTT TAT GTA GAA     1425
Asn Gly Gln Thr Ile Lys Phe Lys Gly Phe Met Thr Leu Tyr Val Glu
405                 410                 415                 420

ACT AAA GAT GAT AGT GAT AGC GAA AAG GAA AAT AAA CTG CCT AAA TTA     1473
Thr Lys Asp Asp Ser Asp Ser Glu Lys Glu Asn Lys Leu Pro Lys Leu
             425                 430                 435

GAG CAA GGT GAT AAA GTC ACA GCA ACT CAA ATT GAA CCA GCT CAA CAC     1521
Glu Gln Gly Asp Lys Val Thr Ala Thr Gln Ile Glu Pro Ala Gln His
         440                 445                 450
```

FIGURE 1C

| | | | | | | | | | | | | | | | |
|---|---|---|---|---|---|---|---|---|---|---|---|---|---|---|---|
| TAT | ACA | CAA | CCA | CCT | CCA | AGA | TAT | ACT | GAG | GCG | AGA | TTA | GTA | AAA | ACA |
| Tyr | Thr | Gln | Pro | Pro | Pro | Arg | Tyr | Thr | Glu | Ala | Arg | Leu | Val | Lys | Thr |
| | | 455 | | | | 460 | | | | | 465 | | | | |

1569

| | | | | | | | | | | | | | | | |
|---|---|---|---|---|---|---|---|---|---|---|---|---|---|---|---|
| CTA | GAA | GAA | TTG | AAA | ATT | GGG | CGA | CCA | TCA | ACT | TAT | GCA | CCG | ACA | ATA |
| Leu | Glu | Glu | Leu | Lys | Ile | Gly | Arg | Pro | Ser | Thr | Tyr | Ala | Pro | Thr | Ile |
| | 470 | | | | | 475 | | | | | 480 | | | | |

1617

| | | | | | | | | | | | | | | | |
|---|---|---|---|---|---|---|---|---|---|---|---|---|---|---|---|
| GAT | ACG | ATT | CAA | AAG | CGT | AAC | TAT | GTC | AAA | TTA | GAA | AGT | AAG | CGT | TTT |
| Asp | Thr | Ile | Gln | Lys | Arg | Asn | Tyr | Val | Lys | Leu | Glu | Ser | Lys | Arg | Phe |
| 485 | | | | 490 | | | | | 495 | | | | | 500 | |

1665

| | | | | | | | | | | | | | | | |
|---|---|---|---|---|---|---|---|---|---|---|---|---|---|---|---|
| GTT | CCT | ACT | GAG | TTG | GGA | GAA | ATA | GTT | CAT | GAA | CAA | GTG | AAA | GAA | TAC |
| Val | Pro | Thr | Glu | Leu | Gly | Glu | Ile | Val | His | Glu | Gln | Val | Lys | Glu | Tyr |
| | | | | 505 | | | | | 510 | | | | | 515 | |

1713

| | | | | | | | | | | | | | | | |
|---|---|---|---|---|---|---|---|---|---|---|---|---|---|---|---|
| TTC | CCA | GAG | ATT | ATT | GAT | GTG | GAA | TTC | ACA | GTG | AAT | ATG | GAA | ACG | TTA |
| Phe | Pro | Glu | Ile | Ile | Asp | Val | Glu | Phe | Thr | Val | Asn | Met | Glu | Thr | Leu |
| | | | | 520 | | | | | 525 | | | | | 530 | |

1761

| | | | | | | | | | | | | | | | |
|---|---|---|---|---|---|---|---|---|---|---|---|---|---|---|---|
| CTT | GAT | AAG | ATT | GCA | GAA | GGC | GAC | ATT | ACA | TGG | AGA | AAA | GTA | ATA | GAC |
| Leu | Asp | Lys | Ile | Ala | Glu | Gly | Asp | Ile | Thr | Trp | Arg | Lys | Val | Ile | Asp |
| | | 535 | | | | | 540 | | | | | 545 | | | |

1809

| | | | | | | | | | | | | | | | |
|---|---|---|---|---|---|---|---|---|---|---|---|---|---|---|---|
| GGT | TTC | TTT | AGT | AGC | TTT | AAA | CAA | GAT | GTT | GAA | CGT | GCT | GAA | GAA | GAG |
| Gly | Phe | Phe | Ser | Ser | Phe | Lys | Gln | Asp | Val | Glu | Arg | Ala | Glu | Glu | Glu |
| | | 550 | | | | | 555 | | | | | 560 | | | |

1857

| | | | | | | | | | | | | | | | |
|---|---|---|---|---|---|---|---|---|---|---|---|---|---|---|---|
| ATG | GAA | AAG | ATT | GAA | ATC | AAA | GAT | GAG | CCA | GCC | GGT | GAA | GAC | TGT | GAA |
| Met | Glu | Lys | Ile | Glu | Ile | Lys | Asp | Glu | Pro | Ala | Gly | Glu | Asp | Cys | Glu |
| 565 | | | | | 570 | | | | | 575 | | | | | 580 |

1905

| | | | | | | | | | | | | | | | |
|---|---|---|---|---|---|---|---|---|---|---|---|---|---|---|---|
| GTT | TGT | GGT | TCT | CCT | ATG | GTT | ATA | AAA | ATG | GGA | CGC | TAT | GGT | AAG | TTC |
| Val | Cys | Gly | Ser | Pro | Met | Val | Ile | Lys | Met | Gly | Arg | Tyr | Gly | Lys | Phe |
| | | | | 585 | | | | | 590 | | | | | 595 | |

1953

| | | | | | | | | | | | | | | | |
|---|---|---|---|---|---|---|---|---|---|---|---|---|---|---|---|
| ATG | GCT | TGC | TCA | AAC | TTC | CCG | GAT | TGT | CGT | AAT | ACA | AAA | GCG | ATA | GTT |
| Met | Ala | Cys | Ser | Asn | Phe | Pro | Asp | Cys | Arg | Asn | Thr | Lys | Ala | Ile | Val |
| | | | | 600 | | | | | 605 | | | | | 610 | |

```
AAG TCT ATT GGT GTT AAA TGT CCA AAA TGT AAT GAT GGT GAC GTC GTA       2049
Lys Ser Ile Gly Val Lys Cys Pro Lys Cys Asn Asp Gly Asp Val Val
        615             620             625

GAA AGA AAA TCT AAA AAG AAT CGT GTC TTT TAT GGA TGT TCG AAA TAT       2097
Glu Arg Lys Ser Lys Lys Asn Arg Val Phe Tyr Gly Cys Ser Lys Tyr
        630             635             640

CCT GAA TGC GAC TTT ATC TCT TGG GAT AAG CCG ATT GGA AGA GAT TGT       2145
Pro Glu Cys Asp Phe Ile Ser Trp Asp Lys Pro Ile Gly Arg Asp Cys
645             650             655             660

CCA AAA TGT AAC CAA TAT CTT GTT GAA AAT AAA AAA GGC AAG ACA ACA       2193
Pro Lys Cys Asn Gln Tyr Leu Val Glu Asn Lys Lys Gly Lys Thr Thr
                665             670             675

CAA GTA ATA TGT TCA AAT TGC GAT TAT AAA GAG GCA GCG CAG AAA TAATAT    2244
Gln Val Ile Cys Ser Asn Cys Asp Tyr Lys Glu Ala Ala Gln Lys
        680             685             690

TTTTATTCCC TAGAGACATT TTAAGATTGT TAAATAGAAT CATTAGTGAA TCTTATTTTA     2304
AAGATAGTAA TGGATTAATC TAAATAAGTG CGGATAATAT AAACATAACA ACATAATTAA     2364
AAGACATAAA TGACAATAAA AGGAGTATAG AAATGACTCA AACTGTAAAT GTAATAGGTG     2424
CTGGTCTTGC CGGTTCAGAA GCGGCATATC AATTAGCTGA AAGAGGAATT AAAGTTAATC     2484
TAATAGAGAT GAGACCTGTT AAACAAACAC CAGCGCACCA TACTGATAAA TTTGCGGAAC     2544
TTGTATGTTC CAATTCATTA CGCGGAAATG CTTTAACTAA TGGTGTGGGT GTTTTAAAAG     2604
AAGAAATGAG AAGATTGAAT TCTATAATTA TTGAAGCGGC TGATAAGGCA CGAGTTCCAG     2664
CTGGTGGTGC ATTAGCAGTT GATAGACACG ATTT                                 2698
```

FIGURE 2. Topoisomerase I predicted amino acid sequence (SEQ ID NO: 2)

```
Met Thr Leu Ala Asp Asn Leu Val Ile Val Glu Ser Pro Ala Lys Ala
 1               5                   10                  15
Lys Thr Ile Glu Lys Tyr Leu Gly Lys Lys Tyr Lys Val Ile Ala Ser
             20                  25                  30
Met Gly His Val Arg Asp Leu Pro Arg Ser Gln Met Gly Val Asp Thr
             35                  40                  45
Glu Asp Asn Tyr Glu Pro Lys Tyr Ile Thr Ile Arg Gly Lys Gly Pro
         50                  55                  60
Val Val Lys Glu Leu Lys Lys His Ala Lys Lys Ala Lys Asn Val Phe
65                  70                  75                  80
Leu Ala Ser Asp Pro Asp Arg Glu Gly Glu Ala Ile Ala Trp His Leu
             85                  90                  95
Ser Lys Ile Leu Glu Leu Glu Asp Ser Lys Glu Asn Arg Val Val Phe
             100                 105                 110
Asn Glu Ile Thr Lys Asp Ala Val Lys Glu Ser Phe Lys Asn Pro Arg
             115                 120                 125
Glu Ile Glu Met Asn Leu Val Asp Ala Gln Gln Ala Arg Arg Ile Leu
             130                 135                 140
Asp Arg Leu Val Gly Tyr Asn Ile Ser Pro Val Leu Trp Lys Lys Val
145                 150                 155                 160
Lys Lys Gly Leu Ser Ala Gly Arg Val Gln Ser Val Ala Leu Arg Leu
             165                 170                 175
Val Ile Asp Arg Glu Asn Glu Ile Arg Asn Phe Lys Pro Glu Glu Tyr
             180                 185                 190
Trp Thr Ile Glu Gly Glu Phe Arg Tyr Lys Lys Ser Lys Phe Asn Ala
             195                 200                 205
Lys Phe Leu His Tyr Lys Asn Lys Pro Phe Lys Leu Lys Thr Lys Lys
             210                 215                 220
Asp Val Glu Lys Ile Thr Ala Ala Leu Asp Gly Asp Gln Phe Glu Ile
225                 230                 235                 240
Thr Asn Val Thr Lys Lys Glu Lys Thr Arg Asn Pro Ala Asn Pro Phe
             245                 250                 255
Thr Thr Ser Thr Leu Gln Gln Glu Ala Ala Arg Lys Leu Asn Phe Lys
             260                 265                 270
Ala Arg Lys Thr Met Met Val Ala Gln Gln Leu Tyr Glu Gly Ile Asp
             275                 280                 285
```

FIGURE 2A

```
Leu Lys Lys Gln Gly Thr Ile Gly Leu Ile Thr Tyr Met Arg Thr Asp
        290                 295                 300
Ser Thr Arg Ile Ser Asp Thr Ala Lys Ala Glu Ala Lys Gln Tyr Ile
305                 310                 315                 320
Thr Asp Lys Tyr Gly Glu Ser Tyr Thr Ser Lys Arg Lys Ala Ser Gly
                325                 330                 335
Lys Gln Gly Asp Gln Asp Ala His Glu Ala Ile Arg Pro Ser Ser Thr
                340                 345                 350
Met Arg Thr Pro Asp Asp Met Lys Ser Phe Leu Thr Lys Asp Gln Tyr
            355                 360                 365
Arg Leu Tyr Lys Leu Ile Trp Glu Arg Phe Val Ala Ser Gln Met Ala
        370                 375                 380
Pro Ala Ile Leu Asp Thr Val Ser Leu Asp Ile Thr Gln Gly Asp Ile
385                 390                 395                 400
Lys Phe Arg Ala Asn Gly Gln Thr Ile Lys Phe Lys Gly Phe Met Thr
                405                 410                 415
Leu Tyr Val Glu Thr Lys Asp Asp Ser Asp Ser Glu Lys Glu Asn Lys
                420                 425                 430
Leu Pro Lys Leu Glu Gln Gly Asp Lys Val Thr Ala Thr Gln Ile Glu
            435                 440                 445
Pro Ala Gln His Tyr Thr Gln Pro Pro Arg Tyr Thr Glu Ala Arg
        450                 455                 460
Leu Val Lys Thr Leu Glu Glu Leu Lys Ile Gly Arg Pro Ser Thr Tyr
465                 470                 475                 480
Ala Pro Thr Ile Asp Thr Ile Gln Lys Arg Asn Tyr Val Lys Leu Glu
                485                 490                 495
Ser Lys Arg Phe Val Pro Thr Glu Leu Gly Glu Ile Val His Glu Gln
                500                 505                 510
Val Lys Glu Tyr Phe Pro Glu Ile Ile Asp Val Glu Phe Thr Val Asn
            515                 520                 525
Met Glu Thr Leu Leu Asp Lys Ile Ala Glu Gly Asp Ile Thr Trp Arg
        530                 535                 540
Lys Val Ile Asp Gly Phe Phe Ser Ser Phe Lys Gln Asp Val Glu Arg
545                 550                 555                 560
Ala Glu Glu Glu Met Glu Lys Ile Glu Ile Lys Asp Glu Pro Ala Gly
                565                 570                 575
Glu Asp Cys Glu Val Cys Gly Ser Pro Met Val Ile Lys Met Gly Arg
                580                 585                 590
```

FIGURE 2B

```
Tyr Gly Lys Phe Met Ala Cys Ser Asn Phe Pro Asp Cys Arg Asn Thr
        595                 600                 605
 Lys Ala Ile Val Lys Ser Ile Gly Val Lys Cys Pro Lys Cys Asn Asp
        610                 615                 620
 Gly Asp Val Val Glu Arg Lys Ser Lys Lys Asn Arg Val Phe Tyr Gly
 625                 630                 635                 640
 Cys Ser Lys Tyr Pro Glu Cys Asp Phe Ile Ser Trp Asp Lys Pro Ile
                645                 650                 655
 Gly Arg Asp Cys Pro Lys Cys Asn Gln Tyr Leu Val Glu Asn Lys Lys
                660                 665                 670
 Gly Lys Thr Thr Gln Val Ile Cys Ser Asn Cys Asp Tyr Lys Glu Ala
        675                 680                 685
 Ala Gln Lys
        690
```

FIGURE 3 Generic sequence encoding Topoisomerase I of SEQ ID NO:2

ATG ACN (CTN or TTR) GCN GAY AAY (CTN or TTR) GTN ATH GTN

GAR (TCN or AGY) CCN GCN AAR GCN AAR ACN ATH GAR

AAR TAY (CTN or TTR) GGN AAR AAR TAY AAR GTN ATH

GCN (TCN or AGY) ATG GGN CAY GTN (CGN or AGR) GAY (CTN or TTR) CCN (CGN or ARG) (TCN or AGY) CAR ATG GGN GTN GAY ACN GAR GAY

AAY TAY GAR CCN AAR TAY ATH ACN ATH (CGN or AGR)

GGN AAR GGN CCN GTN GTN AAR GAR (CTN or TTR) AAR

AAR CAY GCN AAR AAR GCN AAR AAY GTN TTY (CTN or TTR) GCN (TCN or AGY) GAY CCN GAY (CGN or AGR) GAR GCN GAR

GCN ATH GCN TGG CAY (CTN or TTR) (TCN or AGY) AAR ATH (CTN or TTR)

GAR (CTN or TTR) GAR GAY (TCN or AGY) AAR GAR AAY (CGN or AGR) GTN

GTN TTY AAY GAR ATH ACN AAR GAY GCN GTN

AAR GAR (CGN or AGR) TTY AAR AAY CCN (CGN or AGR) GAR ATH

GAR ATG AAY (CTN or TTR) GTN GAY GCN CAR CAR GCN (CGN or AGR) (CGN or AGR) ATH (CTN or TTR) GAY (CGN or AGR) (CTN or TTR) GTN GGN TAY

AAY ATH (TCN or AGY) CCN GTN (CTN or TTR) TGG AAR AAR GTN

AAR AAR GGN (CTN or TTR) (TCN or AGY) GCN GGN (CGN or AGR) GTN CAR

FIGURE 3A (TCN or AGY) GTN GCN (CTN or TTR) (CGN or AGR) (CTN or TTR) GTN ATH GAY (CGN or AGR)

GAR AAY GAR ATH (CGN or AGR) AAY TTY AAR CCN GAR

GAR TAY TGG ACN ATH GAR GGN GAR TTY (CGN or AGR)

TAY AAR AAR (TCN or AGY) AAR TTY AAY GCN AAR TTY (CTN or TTR) CAY TAY AAR AAY AAR CCN TTY AAR (CTN or TTR)

AAR ACN AAR AAR GAY GTN GAR AAR ATH ACN

GCN GCN (CTN or TTR) GAY GGN GAY CAR TTY GAR ATH

ACN AAY GTN ACN AAR AAR GAR AAR ACN (CGN or AGR)

AAY CCN GCN AAY CCN TTY ACN ACN (TCN or AGY) ACN (CTN or TTR) CAR CAR GAR GCN GCN (CGN or AGR) AAR (CTN or TTR) AAY

TTY AAR GCN (CGN or AGR) AAR ACN ATG ATG GTN GCN

CAR CAR (CTN or TTR) TAY GAR GGN ATH GAY (CTN or TTR) AAR

AAR CAR GGN ACN ATH GGN (CTN or TTR) ATH ACN TAY

ATG (CGN or AGR) ACN GAY (TCN or AGY) ACN (CGN or AGR) ATH (TCN or AGY) GAY

ACN GCN AAR GCN GAR GCN AAR CAR TAY ATH

ACN GAY AAR TAY GGN GAR (TCN or AGY) TAY ACN (TCN or AGY)

AAR (CGN or AGR) AAR GCN (TCN or AGY) GGN AAR CAR GGN GAY

CAR GAY GCN CAY GAR GCN ATH (CGN or AGR) CCN (TCN or AGY)

(TCN or AGY) ACN ATG (CGN or AGR) ACN CCN GAY GAY ATG AAR

FIGURE 3B

(TCN or AGY) TTY (CTN or TTR) ACN AAR GAY CAR TAY (CGN or AGR) (CTN or TTR)

TAY AAR (CTN or TTR) ATH TGG GAR (CGN or AGR) TTY GTN GCN (TCN or AGY) CAR ATG GCN CCN GCN ATH (CTN or TTR) GAY ACN

GTN (TCN or AGY) (CTN or TTR) GAY ATH ACN CAR GGN GAY ATH

AAR TTY (CGN or AGR) GCN AAY GGN CAR ACN ATH AAR

TTY AAR GGN TTY ATG ACN (CTN or TTR) TAY GTN GAR

ACN AAR GAY GAY (TCN or AGY) GAY (TCN or AGY) GAR AAR GAR

AAY AAR (CTN or TTR) CCN AAR (CTN or TTR) GAR CAR GGN GAY

AAR GTN ACN GCN ACN CAR ATH GAR CCN GCN

CAR CAY TAY ACN CAR CCN CCN CCN (CGN or AGR) TAY

ACN GAR GCN (CGN or AGR) (CTN or TTR) GTN AAR ACN (CTN or TTR) GAR

GAR (CTN or TTR) AAR ATH GGN (CGN or AGR) CCN (TCN or AGY) ACN TAY

GCN CCN ACN ATH GAY ACN ATH CAR AAR (CGN or AGR)

AAY TAY GTN AAR (CTN or TTR) GAR (TCN or AGY) AAR (CGN or AGR) TTY

GTN CCN ACN GAR (CTN or TTR) GGN GAR ATH GTN CAY

GAR CAR GTN AAR GAR TAY TTY CCN GAR ATH

ATH GAY GTN GAR TTY ACN GTN AAY ATG GAR

ACN (CTN or TTR) (CTN or TTR) GAY AAR ATH GCN GAR GGN GAY

ATH ACN TGG (CGN or AGR) AAR GTN ATH GAY GGN TTY

FIGURE 3C

TTY (TCN or AGY) (TCN or AGY) TTY AAR CAR GAY GTN GAR (CGN or AGR)

GCN GAR GAR GAR ATG GAR AAR ATH GAR ATH

AAR GAY GAR CCN GCN GGN GAR GAY TGY GAR

GTN TGY GGN (TCN or AGY) CCN ATG GTN ATH AAR ATG

GGN (CGN or AGR) TAY GGN AAR TTY ATG GCN TGY (TCN or AGY)

AAY TTY CCN GAY TGY (CGN or AGR) AAY ACN AAR GCN

ATH GTN AAR (TCN or AGY) ATH GGN GTN AAR TGY CCN

AAR TGY AAY GAY GGN GAY GTN GTN GAR (CGN or AGR)

AAR (TCN or AGY) AAR AAR AAY (CGN or AGR) GTN TTY TAY GGN

TGY (TCN or AGY) AAR TAY CCN GAR TGY GAY TTY ATH (TCN or AGY) TGG GAY AAR CCN ATH GGN (CGN or AGR) GAY TGY

CCN AAR TGY AAY CAR TAY (CTN or TTR) GTN GAR AAY

AAR AAR GGN AAR ACN ACN CAR GTN ATH TGY (TCN or AGY) AAY TGY GAY TAY AAR GAR GCN GCN CAR AAR

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 2698 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO:1:

```
ATAACGAGTT GCTTCATATT TCTTTTGTTA CCCTTTGTAA TTTATTTTTT AATAAAATCT      60

ATAAAAAATA GACAGGGAAA ATGATTTGTT TAGATATAAA ACGTTGACAA AAGCAAAATT     120

AAGCGTTTAT CATTTATCTT TAGTAATTAG ATTAGCGAGG GGGAAATGAC ATTGGCAGAT     180

AATTTAGTCA TTGTTGAATC GCCTGCAAAA GCAAAAACCA TTGAAAAGTA TTTAGGTAAG     240

AAATATAAAG TTATAGCTTC AATGGGACAC GTCAGAGACT TACCAAGAAG TCAAATGGGT     300

GTCGACACTG AAGATAATTA CGAACCAAAA TATATAACAA TACGCGGAAA AGGTCCTGTT     360
```

```
GTAAAAGAAT TGAAAAAACA TGCAAAAAAA GCGAAAAACG TCTTTCTCGC AAGTGACCCC     420

GACCGTGAAG GTGAAGCAAT TGCTTGGCAT TTATCAAAAA TTTTAGAGCT TGAAGATTCT     480

AAAGAAAATC GCGTTGTTTT CAACGAAATA ACTAAAGACG CTGTTAAAGA AAGTTTTAAA     540

AATCCTAGAG AAATTGAAAT GAACTTAGTC GATGCACAAC AAGCGCGTCG AATATTAGAT     600

AGATTGGTTG GCTATAACAT CTCGCCAGTT CTATGGAAAA AAGTGAAAAA AGGTTTGTCA     660

GCGGGTCGAG TTCAATCTGT TGCACTTCGT TTAGTCATTG ACCGTGAAAA TGAAATTCGA     720

AACTTTAAAC CAGAAGAATA TTGGACTATT GAAGGAGAAT TTAGATACAA AAAATCAAAA     780

TTCAATGCTA AATTCCTTCA TTATAAAAAT AAACCTTTTA AATTAAAAAC GAAAAAAGAT     840

GTTGAGAAAA TTACAGCTGC ACTAGATGGA GATCAATTCG AAATTACAAA CGTGACTAAA     900

AAAGAAAAAA CGCGTAATCC AGCAAACCCA TTTACAACTT CTACATTACA ACAAGAGGCG     960

GCACGTAAAT TAAACTTTAA AGCAAGAAAA ACAATGATGG TCGCACAACA ATTATATGAA    1020

GGTATAGATT TGAAAAAACA AGGTACGATT GGTTTAATAA CATATATGAG AACCGATTCT    1080

ACACGTATTT CAGATACTGC CAAAGCTGAA GCAAAACAGT ATATAACTGA TAAATACGGT    1140

GAATCTTACA CTTCTAAACG TAAAGCATCA GGGAAACAAG GTGACCAAGA TGCCCATGAG    1200

GCTATTAGAC CTTCAAGTAC TATGCGTACG CCAGATGATA TGAAGTCATT TTTGACGAAA    1260

GACCAATACC GATTATACAA ATTAATTTGG GAACGATTTG TTGCTAGTCA AATGGCTCCA    1320

GCAATACTTG ATACAGTCTC ATTAGACATA ACACAAGGTG ACATTAAATT TAGAGCGAAT    1380

GGTCAAACAA TCAAGTTTAA AGGATTTATG ACACTTTATG TAGAAACTAA AGATGATAGT    1440

GATAGCGAAA AGGAAAATAA ACTGCCTAAA TTAGAGCAAG GTGATAAAGT CACAGCAACT    1500

CAAATTGAAC CAGCTCAACA CTATACACAA CCACCTCCAA GATATACTGA GGCGAGATTA    1560

GTAAAAACAC TAGAAGAATT GAAAATTGGG CGACCATCAA CTTATGCACC GACAATAGAT    1620

ACGATTCAAA AGCGTAACTA TGTCAAATTA GAAAGTAAGC GTTTTGTTCC TACTGAGTTG    1680

GGAGAAATAG TTCATGAACA AGTGAAAGAA TACTTCCCAG AGATTATTGA TGTGGAATTC    1740

ACAGTGAATA TGGAAACGTT ACTTGATAAG ATTGCAGAAG GCGACATTAC ATGGAGAAAA    1800

GTAATAGACG GTTTCTTTAG TAGCTTTAAA CAAGATGTTG AACGTGCTGA AGAAGAGATG    1860

GAAAAGATTG AAATCAAAGA TGAGCCAGCC GGTGAAGACT GTGAAGTTTG TGGTTCTCCT    1920

ATGGTTATAA AAATGGGACG CTATGGTAAG TTCATGGCTT GCTCAAACTT CCCGGATTGT    1980

CGTAATACAA AAGCGATAGT TAAGTCTATT GGTGTTAAAT GTCCAAAATG TAATGATGGT    2040

GACGTCGTAG AAAGAAAATC TAAAAAGAAT CGTGTCTTTT ATGGATGTTC GAAATATCCT    2100

GAATGCGACT TTATCTCTTG GGATAAGCCG ATTGGAAGAG ATTGTCCAAA ATGTAACCAA    2160

TATCTTGTTG AAAATAAAAA AGGCAAGACA ACACAAGTAA TATGTTCAAA TTGCGATTAT    2220

AAAGAGGCAG CGCAGAAATA ATATTTTTAT TCCCTAGAGA CATTTTAAGA TTGTTAAATA    2280

GAATCATTAG TGAATCTTAT TTTAAAGATA GTAATGGATT AATCTAAATA AGTGCGGATA    2340

ATATAAACAT AACAACATAA TTAAAAGACA TAAATGACAA TAAAAGGAGT ATAGAAATGA    2400

CTCAAACTGT AAATGTAATA GGTGCTGGTC TTGCCGGTTC AGAAGCGGCA TATCAATTAG    2460

CTGAAAGAGG AATTAAAGTT AATCTAATAG AGATGAGACC TGTTAAACAA ACACCAGCGC    2520

ACCATACTGA TAAATTTGCG GAACTTGTAT GTTCCAATTC ATTACGCGGA AATGCTTTAA    2580

CTAATGGTGT GGGTGTTTTA AAAGAAGAAA TGAGAAGATT GAATTCTATA ATTATTGAAG    2640

CGGCTGATAA GGCACGAGTT CCAGCTGGTG GTGCATTAGC AGTTGATAGA CACGATTT     2698
```

(2) INFORMATION FOR SEQ ID NO:2:

(i) SEQUENCE CHARACTERISTICS:
        (A) LENGTH: 691 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Thr Leu Ala Asp Asn Leu Val Ile Val Glu Ser Pro Ala Lys Ala
 1               5                  10                  15

Lys Thr Ile Glu Lys Tyr Leu Gly Lys Lys Tyr Lys Val Ile Ala Ser
                20                  25                  30

Met Gly His Val Arg Asp Leu Pro Arg Ser Gln Met Gly Val Asp Thr
            35                  40                  45

Glu Asp Asn Tyr Glu Pro Lys Tyr Ile Thr Ile Arg Gly Lys Gly Pro
        50                  55                  60

Val Val Lys Glu Leu Lys Lys His Ala Lys Ala Lys Asn Val Phe
 65                  70                  75                  80

Leu Ala Ser Asp Pro Asp Arg Glu Gly Glu Ala Ile Ala Trp His Leu
                85                  90                  95

Ser Lys Ile Leu Glu Leu Glu Asp Ser Lys Glu Asn Arg Val Val Phe
               100                 105                 110

Asn Glu Ile Thr Lys Asp Ala Val Lys Glu Ser Phe Lys Asn Pro Arg
            115                 120                 125

Glu Ile Glu Met Asn Leu Val Asp Ala Gln Gln Ala Arg Arg Ile Leu
        130                 135                 140

Asp Arg Leu Val Gly Tyr Asn Ile Ser Pro Val Leu Trp Lys Lys Val
145                 150                 155                 160

Lys Lys Gly Leu Ser Ala Gly Arg Val Gln Ser Val Ala Leu Arg Leu
                165                 170                 175

Val Ile Asp Arg Glu Asn Glu Ile Arg Asn Phe Lys Pro Glu Glu Tyr
            180                 185                 190

Trp Thr Ile Glu Gly Glu Phe Arg Tyr Lys Lys Ser Lys Phe Asn Ala
        195                 200                 205

Lys Phe Leu His Tyr Lys Asn Lys Pro Phe Lys Leu Lys Thr Lys Lys
    210                 215                 220

Asp Val Glu Lys Ile Thr Ala Ala Leu Asp Gly Asp Gln Phe Glu Ile
225                 230                 235                 240

Thr Asn Val Thr Lys Lys Glu Lys Thr Arg Asn Pro Ala Asn Pro Phe
                245                 250                 255

Thr Thr Ser Thr Leu Gln Gln Glu Ala Ala Arg Lys Leu Asn Phe Lys
            260                 265                 270

Ala Arg Lys Thr Met Met Val Ala Gln Gln Leu Tyr Glu Gly Ile Asp
        275                 280                 285

Leu Lys Lys Gln Gly Thr Ile Gly Leu Ile Thr Tyr Met Arg Thr Asp
    290                 295                 300

Ser Thr Arg Ile Ser Asp Thr Ala Lys Ala Glu Ala Lys Gln Tyr Ile
305                 310                 315                 320

Thr Asp Lys Tyr Gly Glu Ser Tyr Ser Lys Arg Lys Ala Ser Gly
                325                 330                 335

Lys Gln Gly Asp Gln Asp Ala His Glu Ala Ile Arg Pro Ser Ser Thr
            340                 345                 350

Met Arg Thr Pro Asp Asp Met Lys Ser Phe Leu Thr Lys Asp Gln Tyr
```

```
            355                 360                 365
Arg Leu Tyr Lys Leu Ile Trp Glu Arg Phe Val Ala Ser Gln Met Ala
370                 375                 380

Pro Ala Ile Leu Asp Thr Val Ser Leu Asp Ile Thr Gln Gly Asp Ile
385                 390                 395                 400

Lys Phe Arg Ala Asn Gly Gln Thr Ile Lys Phe Lys Gly Phe Met Thr
                405                 410                 415

Leu Tyr Val Glu Thr Lys Asp Asp Ser Asp Ser Glu Lys Glu Asn Lys
                420                 425                 430

Leu Pro Lys Leu Glu Gln Gly Asp Lys Val Thr Ala Thr Gln Ile Glu
                435                 440                 445

Pro Ala Gln His Tyr Thr Gln Pro Pro Arg Tyr Thr Glu Ala Arg
450                 455                 460

Leu Val Lys Thr Leu Glu Glu Leu Lys Ile Gly Arg Pro Ser Thr Tyr
465                 470                 475                 480

Ala Pro Thr Ile Asp Thr Ile Gln Lys Arg Asn Tyr Val Lys Leu Glu
                485                 490                 495

Ser Lys Arg Phe Val Pro Thr Glu Leu Gly Glu Ile Val His Glu Gln
                500                 505                 510

Val Lys Glu Tyr Phe Pro Glu Ile Ile Asp Val Glu Phe Thr Val Asn
                515                 520                 525

Met Glu Thr Leu Leu Asp Lys Ile Ala Glu Gly Asp Ile Thr Trp Arg
530                 535                 540

Lys Val Ile Asp Gly Phe Phe Ser Ser Phe Lys Gln Asp Val Glu Arg
545                 550                 555                 560

Ala Glu Glu Glu Met Glu Lys Ile Glu Ile Lys Asp Glu Pro Ala Gly
                565                 570                 575

Glu Asp Cys Glu Val Cys Gly Ser Pro Met Val Ile Lys Met Gly Arg
                580                 585                 590

Tyr Gly Lys Phe Met Ala Cys Ser Asn Phe Pro Asp Cys Arg Asn Thr
                595                 600                 605

Lys Ala Ile Val Lys Ser Ile Gly Val Lys Cys Pro Lys Cys Asn Asp
610                 615                 620

Gly Asp Val Val Glu Arg Lys Ser Lys Asn Arg Val Phe Tyr Gly
625                 630                 635                 640

Cys Ser Lys Tyr Pro Glu Cys Asp Phe Ile Ser Trp Asp Lys Pro Ile
                645                 650                 655

Gly Arg Asp Cys Pro Lys Cys Asn Gln Tyr Leu Val Glu Asn Lys Lys
                660                 665                 670

Gly Lys Thr Thr Gln Val Ile Cys Ser Asn Cys Asp Tyr Lys Glu Ala
                675                 680                 685

Ala Gln Lys
    690

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:3:

GGGGAAATGA CATTGGCAGA TA                                              22
```

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:4:

```
TCTTAAAATG TCTCTAGGGA ATAA                                           24
```

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:5:

```
ACGAAATAAC TAAAGACGCT GTTAAAG                                        27
```

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:6:

```
GCGAGATGTT ATAGCCAACC AATC                                           24
```

(2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:7:

```
ACTTAGTCGA TGCACAACAA GCGCGT                                         26
```

(2) INFORMATION FOR SEQ ID NO:8:

(i) SEQUENCE CHARACTERISTICS:
        (A) LENGTH: 2136 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:8:

```
ATGGGCAGCA GCCATCATCA TCATCATCAC AGCAGCGGCC TGGTGCCGCG CGGCAGCCAT     60

ATGACCTTGG CAGATAATTT AGTCATTGTT GAATCGCCTG CAAAAGCAAA AACCATTGAA    120

AAGTATTTAG GTAAGAAATA TAAAGTTATA GCTTCAATGG GACACGTCAG AGACTTACCA    180
```

```
AGAAGTCAAA TGGGTGTCGA CACTGAAGAT AATTACGAAC CAAAATATAT AACAATACGC   240

GGAAAAGGTC CTGTTGTAAA AGAATTGAAA AAACATGCAA AAAAAGCGAA AAACGTCTTT   300

CTCGCAAGTG ACCCCGACCG TGAAGGTGAA GCAATTGCTT GGCATTTATC AAAAATTTTA   360

GAGCTTGAAG ATTCTAAAGA AAATCGCGTT GTTTTCAACG AAATAACTAA AGACGCTGTT   420

AAAGAAAGTT TTAAAAATCC TAGAGAAATT GAAATGAACT TAGTCGATGC ACAACAAGCG   480

CGTCGAATAT TAGATAGATT GGTTGGCTAT AACATCTCGC CAGTTCTATG GAAAAAAGTG   540

AAAAAAGGTT TGTCAGCGGG TCGAGTTCAA TCTGTTGCAC TTCGTTTAGT CATTGACCGT   600

GAAAATGAAA TTCGAAACTT TAAACCAGAA GAATATTGGA CTATTGAAGG AGAATTTAGA   660

TACAAAAAAT CAAAATTCAA TGCTAAATTC CTTCATTATA AAAATAAACC TTTTAAATTA   720

AAAACGAAAA AAGATGTTGA GAAAATTACA GCTGCACTAG ATGGAGATCA ATTCGAAATT   780

ACAAACGTGA CTAAAAAAGA AAAAACGCGT AATCCAGCAA ACCCATTTAC AACTTCTACA   840

TTACAACAAG AGGCGGCACG TAAATTAAAC TTTAAAGCAA GAAAACAAT GATGGTCGCA    900

CAACAATTAT ATGAAGGTAT AGATTTGAAA AACAAGGTA CGATTGGTTT AATAACATAT    960

ATGAGAACCG ATTCTACACG TATTTCAGAT ACTGCCAAAG CTGAAGCAAA ACAGTATATA  1020

ACTGATAAAT ACGGTGAATC TTACACTTCT AAACGTAAAG CATCAGGGAA ACAAGGTGAC  1080

CAAGATGCCC ATGAGGCTAT TAGACCTTCA AGTACTATGC GTACGCCAGA TGATATGAAG  1140

TCATTTTTGA CGAAAGACCA ATACCGATTA TACAAATTAA TTTGGGAACG ATTTGTTGCT  1200

AGTCAAATGG CTCCAGCAAT ACTTGATACA GTCTCATTAG ACATAACACA AGGTGACATT  1260

AAATTTAGAG CGAATGGTCA AACAATCAAG TTTAAAGGAT TTATGACACT TTATGTAGAA  1320

ACTAAAGATG ATAGTGATAG CGAAAAGGAA AATAAACTGC CTAAATTAGA GCAAGGTGAT  1380

AAAGTCACAG CAACTCAAAT TGAACCAGCT CAACACTATA CACAACCACC TCCAAGATAT  1440

ACTGAGGCGA GATTAGTAAA AACACTAGAA GAATTGAAAA TTGGGCGACC ATCAACTTAT  1500

GCACCGACAA TAGATACGAT TCAAAAGCGT AACTATGTCA AATTAGAAAG TAAGCGTTTT  1560

GTTCCTACTG AGTTGGGAGA AATAGTTCAT GAACAAGTGA AGAATACTT CCCAGAGATT   1620

ATTGATGTGG AATTCACAGT GAATATGGAA ACGTTACTTG ATAAGATTGC AGAAGGCGAC  1680

ATTACATGGA GAAAAGTAAT AGACGGTTTC TTTAGTAGCT TTAAACAAGA TGTTGAACGT  1740

GCTGAAGAAG AGATGGAAAA GATTGAAATC AAAGATGAGC CAGCCGGTGA AGACTGTGAA  1800

GTTTGTGGTT CTCCTATGGT TATAAAAATG GGACGCTATG GTAAGTTCAT GGCTTGCTCA  1860

AACTTCCCGG ATTGTCGTAA TACAAAAGCG ATAGTTAAGT CTATTGGTGT TAAATGTCCA  1920

AAATGTAATG ATGGTGACGT CGTAGAAAGA AAATCTAAAA AGAATCGTGT CTTTTATGGA  1980

TGTTCGAAAT ATCCTGAATG CGACTTTATC TCTTGGGATA AGCCGATTGG AAGAGATTGT  2040

CCAAAATGTA ACCAATATCT TGTTGAAAAT AAAAAAGGCA AGACAACACA AGTAATATGT  2100

TCAAATTGCG ATTATAAAGA GGCAGCGCAG AAATAA                            2136
```

(2) INFORMATION FOR SEQ ID NO:9:

(i) SEQUENCE CHARACTERISTICS:
        (A) LENGTH: 711 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

-continued

```
Met Gly Ser Ser His His His His His His Ser Ser Gly Leu Val Pro
 1               5                  10                  15

Arg Gly Ser His Met Thr Leu Ala Asp Asn Leu Val Ile Val Glu Ser
             20                  25                  30

Pro Ala Lys Ala Lys Thr Ile Glu Lys Tyr Leu Gly Lys Lys Tyr Lys
         35                  40                  45

Val Ile Ala Ser Met Gly His Val Arg Asp Leu Pro Arg Ser Gln Met
     50                  55                  60

Gly Val Asp Thr Glu Asp Asn Tyr Glu Pro Lys Tyr Ile Thr Ile Arg
 65                  70                  75                  80

Gly Lys Gly Pro Val Val Lys Glu Leu Lys Lys His Ala Lys Lys Ala
                 85                  90                  95

Lys Asn Val Phe Leu Ala Ser Asp Pro Asp Arg Glu Gly Glu Ala Ile
            100                 105                 110

Ala Trp His Leu Ser Lys Ile Leu Glu Leu Glu Asp Ser Lys Glu Asn
            115                 120                 125

Arg Val Val Phe Asn Glu Ile Thr Lys Asp Ala Val Lys Glu Ser Phe
        130                 135                 140

Lys Asn Pro Arg Glu Ile Glu Met Asn Leu Val Asp Ala Gln Gln Ala
145                 150                 155                 160

Arg Arg Ile Leu Asp Arg Leu Val Gly Tyr Asn Ile Ser Pro Val Leu
                165                 170                 175

Trp Lys Lys Val Lys Lys Gly Leu Ser Ala Gly Arg Val Gln Ser Val
                180                 185                 190

Ala Leu Arg Leu Val Ile Asp Arg Glu Asn Glu Ile Arg Asn Phe Lys
        195                 200                 205

Pro Glu Glu Tyr Trp Thr Ile Glu Gly Glu Phe Arg Tyr Lys Lys Ser
    210                 215                 220

Lys Phe Asn Ala Lys Phe Leu His Tyr Lys Asn Lys Pro Phe Lys Leu
225                 230                 235                 240

Lys Thr Lys Lys Asp Val Glu Lys Ile Thr Ala Ala Leu Asp Gly Asp
                245                 250                 255

Gln Phe Glu Ile Thr Asn Val Thr Lys Lys Glu Lys Thr Arg Asn Pro
            260                 265                 270

Ala Asn Pro Phe Thr Thr Ser Thr Leu Gln Gln Glu Ala Ala Arg Lys
        275                 280                 285

Leu Asn Phe Lys Ala Arg Lys Thr Met Met Val Ala Gln Gln Leu Tyr
    290                 295                 300

Glu Gly Ile Asp Leu Lys Lys Gln Gly Thr Ile Gly Leu Ile Thr Tyr
305                 310                 315                 320

Met Arg Thr Asp Ser Thr Arg Ile Ser Asp Thr Ala Lys Ala Glu Ala
                325                 330                 335

Lys Gln Tyr Ile Thr Asp Lys Tyr Gly Glu Ser Tyr Thr Ser Lys Arg
            340                 345                 350

Lys Ala Ser Gly Lys Gln Gly Asp Gln Asp Ala His Glu Ala Ile Arg
        355                 360                 365

Pro Ser Ser Thr Met Arg Thr Pro Asp Asp Met Lys Ser Phe Leu Thr
    370                 375                 380

Lys Asp Gln Tyr Arg Leu Tyr Lys Leu Ile Trp Glu Arg Phe Val Ala
385                 390                 395                 400

Ser Gln Met Ala Pro Ala Ile Leu Asp Thr Val Ser Leu Asp Ile Thr
                405                 410                 415
```

-continued

```
Gln Gly Asp Ile Lys Phe Arg Ala Asn Gly Gln Thr Ile Lys Phe Lys
            420                 425                 430
Gly Phe Met Thr Leu Tyr Val Glu Thr Lys Asp Asp Ser Asp Ser Glu
            435                 440                 445
Lys Glu Asn Lys Leu Pro Lys Leu Glu Gln Gly Asp Lys Val Thr Ala
            450                 455                 460
Thr Gln Ile Glu Pro Ala Gln His Tyr Thr Gln Pro Pro Arg Tyr
465             470                 475                 480
Thr Glu Ala Arg Leu Val Lys Thr Leu Glu Glu Leu Lys Ile Gly Arg
                485                 490                 495
Pro Ser Thr Tyr Ala Pro Thr Ile Asp Thr Ile Gln Lys Arg Asn Tyr
            500                 505                 510
Val Lys Leu Glu Ser Lys Arg Phe Val Pro Thr Glu Leu Gly Glu Ile
            515                 520                 525
Val His Glu Gln Val Lys Glu Tyr Phe Pro Glu Ile Ile Asp Val Glu
            530                 535                 540
Phe Thr Val Asn Met Glu Thr Leu Leu Asp Lys Ile Ala Glu Gly Asp
545             550                 555                 560
Ile Thr Trp Arg Lys Val Ile Asp Gly Phe Phe Ser Ser Phe Lys Gln
                565                 570                 575
Asp Val Glu Arg Ala Glu Glu Met Glu Lys Ile Glu Ile Lys Asp
            580                 585                 590
Glu Pro Ala Gly Glu Asp Cys Glu Val Cys Gly Ser Pro Met Val Ile
            595                 600                 605
Lys Met Gly Arg Tyr Gly Lys Phe Met Ala Cys Ser Asn Phe Pro Asp
    610                 615                 620
Cys Arg Asn Thr Lys Ala Ile Val Lys Ser Ile Gly Val Lys Cys Pro
625                 630                 635                 640
Lys Cys Asn Asp Gly Asp Val Val Glu Arg Lys Ser Lys Lys Asn Arg
                645                 650                 655
Val Phe Tyr Gly Cys Ser Lys Tyr Pro Glu Cys Asp Phe Ile Ser Trp
            660                 665                 670
Asp Lys Pro Ile Gly Arg Asp Cys Pro Lys Cys Asn Gln Tyr Leu Val
            675                 680                 685
Glu Asn Lys Lys Gly Lys Thr Thr Gln Val Ile Cys Ser Asn Cys Asp
        690                 695                 700
Tyr Lys Glu Ala Ala Gln Lys
705                 710
```

(2) INFORMATION FOR SEQ ID NO:10:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

```
Met Gly Ser Ser His His His His His His Ser Ser Gly Leu Val Pro
1               5                   10                  15
Arg
```

(2) INFORMATION FOR SEQ ID NO:11:

(i) SEQUENCE CHARACTERISTICS:

```
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:11:

GAATGAGCCG CAACTTCGGG AT                                                    22

(2) INFORMATION FOR SEQ ID NO:12:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:12:

GACATTGGCA GATAATTTAG TCATTGTTGA ATCGCCTGC                                  39

(2) INFORMATION FOR SEQ ID NO:13:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:13:

GTTCAAATTG CGATTATAAA GAGGCAGCGC AG                                         32
```

TOPOISOMERASE I

RELATED APPLICATION

This application is a divisional of U.S. Application Ser. No. 08/946,475, filed Oct. 7, 1997, now U.S. Pat. No. 6,013,505, and claims benefit under 35 USC 199(e) of U.S. Provisional Application Ser. No. 60/027,973, filed on Oct. 8, 1996.

This invention relates, in part, to newly identified polynucleotides and polypeptides; variants and derivatives of these polynucleotides and polypeptides; processes for making these polynucleotides and these polypeptides, and their variants and derivatives; agonists and antagonists of the polypeptides; and uses of these polynucleotides, polypeptides, variants, derivatives, agonists and antagonists. In particular, in these and in other regards, the invention relates to polynucleotides and polypeptides of bacterial "Topoisomerase I".

BACKGROUND OF THE INVENTION

Among the more effective antibiotics are those that interfere with common modes of bacterial gene expression, regulation or activity. Recently, the supercoiling of DNA had been suggested as a possible mode of virulence gene regulation. Local increases or decreases in DNA density, due to supercoiling, have been associated with responses to various environmental conditions such as, temperature, anaerobiosis, and osmolarity. Appropriate regulation of the accessibility of groups of genes to components of the transcriptional apparatus by increasing or decreasing supercoiling of spatially organized genes may represent an infecting pathogen's effective response to such environmental conditions. Enzymes, such as DNA topoisomerases including type I topoisomerases and DNA gyrases, have been identified which function to effect the levels of DNA supercoiling. Such enzymes represent useful targets against which to screen compounds as potential antibiotics.

DNA transformations performed by DNA topoisomerases are accomplished by the cleavage of either a single strand or both strands. The unit change in the Linking number (Lk) resulting from such transformations is the best operational distinction between the two classes of topoisomerases (P. O. Brown & N. R. Cozzarelli, *Science* 206:1081–1083 (1979)). The linking number (Lk) is the algebraic number of times one strand crosses the surface stretched over the other strand. DNA topoisomerases whose reactions proceed via a transient single-stranded break and changing the Lk in steps of one are classified as type 1, while enzymes whose reactions proceed via double-stranded breaks and changing the Lk in steps of two are classified as type 2.

Members of type 2 topoisomerase family include DNA gyrase, bacterial DNA topoisomerase IV, T-even phage DNA topoisomerases, eukaryotic DNA topoisomerase II, and thermophilic topoisomerase II from *Sulfolobus acidocaldarius* (see: A. Kikuchi et al., *Syst. Appl. Microbiol.* 7: 72–78 (1986); J. Kato et al, *J. Biol. Chem.* 267: 25676–25684 (1992); W. M. Huang in DNA Topology and Its Biological Effects (N. R. Cozzarelli and J. C. Wang, eds., Cold Spring Harbor Laboratory Press, New York, 1990), pp. 265–284; T.-S Hsieh in DNA Topology and Its Biological Effects (N. R. Cozzarelli and J. C. Wang, eds., Cold Spring Harbor Laboratory Press, New York, (1990), pp. 243–263)). The coding sequences of a dozen or so type 2 enzymes have been determined, and the data suggest that all these enzymes are evolutionary and structurally related. Topological reactions catalyzed by type 2 topoisomerases include introduction of negative supercoils into DNA (DNA gyrase), relaxation of supercoiled DNA, catenation (or decatenation) of duplex circles, knotting and unknotting of DNA.

The family of type 1 topoisomerases comprises bacterial topoisomerase I, *E. coli* topoisomerase III, *S. cerevisiae* topoisomerase III (R. A. Kim & J. C. Wang. *J. Biol. Chem.* 267: 17178–17185 (1992), human topoisomerase III (Hanai et al., *Proc. Natl. Acad. Sci.* 93:3653–3657 (1996)), the type 1 topoisomerase from chloroplasts that closely resembles bacterial enzymes (J. Siedlecki et al, *Nucleic Acids Res.* 11: 1523–1536 (1983), thermophilic reverse gyrases (A. Kikuchi, In DNA: "Topology and Its Biological Effects" (N. R. Cozzarelli and J. C. Wang, eds., Cold Spring Harbor Laboratory Press, New York, 1990, pp. 285–298); C. Bouthier de la Tour et al., *J. Bact.* 173: 3921–3923 (1991), thermophilic *D. amylolyticus* topoisomerase III (A. I. Slesarev et al., *J. Biol. Chem.* 266: 12321–12328 (1991), nuclear topoisomerases I and closely related enzymes from mitochondria and poxviruses (N. Osheroff, *Pharmac. Ther.* 41: 223–241 (1989)). With respect to the mechanism of catalysis these topoisomerases can be divided into two groups.

Group A consists of enzymes that require a divalent cation for activity, and form a transient covalent complex with the 5'-phosphoryl termini (prokaryotic type 1 topoisomerases, *S. cerevisiae* topoisomerase III, and human topoisomerase III). Group B includes type 1 topoisomerases that do not require a divalent cation for activity, and bind covalently to the 3'-phosphoryl termini (nuclear topoisomerases 1, enzymes from mitochondria and poxviruses commonly called eukaryotic topoisomerases I). Type I topoisomerases can carry out the following topological reactions: they relax supercoiled DNA (except of reverse gyrases), catenate (or decatenate) single-stranded circular DNAs or duplexes providing that at least one of the molecules contains a nick or gap, or interact with single-stranded circles to introduce topological knots (type 1-group A topoisomerases). Reverse gyrase, belonging to type 1-group A topoisomerases, is the only topoisomerase shown to be able to introduce positive supercoils into cDNA.

Research on DNA topoisomerases has progressed from DNA enzymology to developmental therapeutics. Bacterial DNA topoisomerase II is an important therapeutic target of quinolone antibiotics; mammalian DNA topoisomerase II is the cellular target of many potent antitumor drugs (K. Drlica, *Microbiol. Rev.* 48: 273–289 (1984) and *Biochemistry* 27: 2253–2259 (1988); B. S. Glisson & W. E. Ross, *Pharmacol. Ther.* 32: 89–106 (1987); A. L. Bodley & L. F. Liu, *Biotechnology* 6: 1315–1319 (1988); L. F. Liu, *Annu. Rev. Biochem.* 58: 351–375 (1989)). These drugs, referred to as topoisomerase II poisons, interfere with the breakage-rejoining reaction of type II topoisomerase by trapping a key covalent reaction intermediate, termed the cleavable complex. Mammalian topoisomerase I is the cellular target of the antitumor drug topotecan (U.S. Pat. No. 5,004,758), which also traps the covalent reaction intermediate.

As mentioned above, bacterial type I topoisomerases (topoisomerase I & III) are enzymes that alter DNA topology and are involved in a number of crucial cellular processes including replication, transcription and recombination (Luttinger, A., *Molecular Microbiol.* 15(4):601–608 (1995). These enzymes act by transiently breaking one strand of DNA, passing a single or double strand of DNA through the break and finally resealing the break. Cleavage of the DNA substrate forms a covalent linkage between a tyrosine residue of the enzyme and the 5' end of the DNA chain at the cleavage site (Roca, J. A., *TIBS* 20:156–160 (1995).

Enzyme inhibition which leads to the stabilization of the covalent-enzyme-DNA complex (cleavable complex), will invoke chromosomal damage, and bacterial cell death. Furthermore, this mechanism has the potential of leading to cell death by virtue of a single inhibition event. A small molecular weight inhibitor, which acts by stabilization of the cleavable complex may act on both topoisomerase I and III because of the extensive amino acid sequence similarity between them, particularly in the region of their active sites. The likelihood of future high level resistance to such agents arising from point mutation may therefore be low.

Inhibitors of type I topoisomerases, for example, those able to stabilize the protein in a covalent complex with DNA would be lethal or inhibitory to the bacterium and thereby have utility in anti-bacterial therapy. It is particularly preferred to employ Staphylococcal genes and gene products as targets for the development of antibiotics. The Staphylococci make up a medically important genera of microbes. They are known to produce two types of disease, invasive and toxigenic. Invasive infections are characterized generally by abscess formation effecting both skin surfaces and deep tissues. *S. aureus* is the second leading cause of bacteremia in cancer patients. Osteomyelitis, septic arthritis, septic thrombophlebitis and acute bacterial endocarditis are also relatively common. There are at least three clinical conditions resulting from the toxigenic properties of Staphylococci. The manifestation of these diseases result from the actions of exotoxins as opposed to tissue invasion and bacteremia. These conditions include: Staphylococcal food poisoning, scalded skin syndrome and toxic shock syndrome.

SUMMARY OF THE INVENTION

Toward these ends, and others, it is an object of the present invention to provide polypeptides, inter alia, that have been identified as novel Topoisomerase I by homology between the amino acid sequence set out in FIG. 2 (SEQ ID NO:2) and known amino acid sequences of other proteins such as *Bacillus subtilis* topoisomerase I which is 68% identical and 80% similar to the sequence in FIG. 2.

It is a further object of the invention, moreover, to provide polynucleotides that encode Topoisomerase L particularly polynucleotides that encode the polypeptide herein designated bacterial Topoisomerase I.

In a particularly preferred embodiment of this aspect of the invention the polynucleotide comprises the region encoding Topoisomerase I in the sequence set out in FIG. 1 (SEQ ID NO:1).

In another particularly preferred embodiment of the present invention there is a novel Topoisomerase I protein from *Staphylococcus aureus* comprising the amino acid sequence of (SEQ ID NO:2), or a fragment, analogue or derivative thereof.

In accordance with this aspect of the present invention there is provided an isolated nucleic acid molecule encoding a mature polypeptide expressible by the *Staphylococcus aurues* polynucleotide contained in deposited strain NCIMB 40771.

In accordance with this aspect of the invention there are provided isolated nucleic acid molecules encoding Topoisomerase I, particularly Staphylococcal Topoisomerase L including mRNAs, cDNAs, genomic DNAs and, in further embodiments of this aspect of the invention, biologically, diagnostically, clinically or therapeutically useful variants, analogs or derivatives thereof, or fragments thereof, including fragments of the variants, analogs and derivatives.

Among the particularly preferred embodiments of this aspect of the invention are naturally occurring allelic variants of Topoisomerase I.

In accordance with this aspect of the invention there are provided novel polypeptides of Staphylococcal origin referred to herein as Topoisomerase I as well as biologically, diagnostically or therapeutically useful fragments thereof, as well as variants, derivatives and analogs of the foregoing and fragments thereof.

It also is an object of the invention to provide Topoisomerase I polypeptides, particularly bacterial Topoisomerase I polypeptides, that may be employed for therapeutic purposes, for example, to treat disease, including treatment by conferring host immunity against bacterial infections, such as Staphylococcal infections.

In accordance with yet a further aspect of the present invention, there is provided the use of a polypeptide of the invention, in particular a fragment thereof, for therapeutic or prophylactic purposes, for example, as an antibacterial agent or a vaccine.

In accordance with another aspect of the present invention, there is provided the use of a polynucleotide of the invention for therapeutic or prophylactic purposes, in particular genetic immunization.

Among the particularly preferred embodiments of this aspect of the invention are variants of Topoisomerase I polypeptide encoded by naturally occurring alleles of the Topoisomerase I gene.

It is another object of the invention to provide a process for producing the aforementioned polypeptides, polypeptide fragments, variants and derivatives, fragments of the variants and derivatives, and analogs of the foregoing.

In a preferred embodiment of this aspect of the invention there are provided methods for producing the aforementioned Topoisomerase I polypeptides comprising culturing host cells having expressibly incorporated therein an exogenously-derived Topoisomerase I-encoding polynucleotide under conditions for expression of Topoisomerase I in the host and then recovering the expressed polypeptide.

In accordance with another object the invention there are provided products, compositions, processes and methods that utilize the aforementioned polypeptides and polynucleotides, inter alia, for research, biological, clinical and therapeutic purposes.

In accordance with yet another aspect of the present invention, there are provided inhibitors of such polypeptides, useful as antibacterial agents. In particular, there are provided antibodies against such polypeptides.

In accordance with certain preferred embodiments of this and other aspects of the invention there are probes that hybridize to bacterial Topoisomerase I sequences useful for detection of bacterial infection.

In certain additional preferred embodiments of this aspect of the invention there are provided antibodies against Topoisomerase I polypeptides. In certain particularly preferred embodiments in this regard, the antibodies are selective for Staphylococcal Topoisomerase I.

In accordance with another aspect of the present invention, there are provided Topoisomerase I agonists. Among preferred agonists are molecules that mimic Topoisomerase I, that bind to Topoisomerase I-binding molecules, and that elicit or augment Topoisomerase I-induced responses. Also among preferred agonists are molecules that interact with Topoisomerase I encoding genes or Topoisomerase I polypeptides, or with other modulators of Topoisomerase I activities, and thereby potentiate or augment an effect of Topoisomerase I or more than one effect of Topoisomerase I and which are also preferably bacteriostatic or bacteriocidal.

In accordance with yet another aspect of the present invention, there are provided Topoisomerase I antagonists. Among preferred antagonists are those which bind to Topoisomerase I so as to inhibit the binding of Topoisomerase I-binding molecules or to stabilize the complex formed between Topoisomerase I and Topoisomerase I binding molecule to prevent further biological activity arising from the Topoisomerase I. Also among preferred antagonists are molecules that bind to or interact with Topoisomerase I so as to inhibit an effect of Topoisomerase I or more than one effect of Topoisomerase I or which prevent expression of Topoisomerase I and which are also preferably bacteriostatic or bacteriocidal.

In a further aspect of the invention there are provided compositions comprising a Topoisomerase I polynucleotide or a Topoisomerase I polypeptide for administration to cells in vitro, to cells ex vivo and to cells in vivo, or to a multicellular organism. In certain preferred embodiments of this aspect of the invention, the compositions comprise a Topoisomerase I polynucleotide for expression of a Topoisomerase I polypeptide in a host organism to raise an immunological response, preferably to raise immunity in such host against Staphylococci or related organisms.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIG. 1 shows the polynucleotide sequence of *Staphylococcus aureus* Topoisomerase I (SEQ ID NO:1).

FIG. 2 shows the amino acid sequence of *Staphylococcus aureus* Topoisomerase I (SEQ ID NO:2) deduced from the polynucleotide sequence of FIG. 1 (SEQ ID NO:1).

FIG. 3 illustrates a generic formula for nucleic acids encoding the Topoisomerase I of (SEQ ID NO:2).

GLOSSARY

The following illustrative explanations are provided to facilitate understanding of certain terms used frequently herein, particularly in the Examples. The explanations are provided as a convenience and are not limitative of the invention.

Topoisomerase I-BINDING MOLECULE, as used herein, refers to molecules or ions which bind or interact specifically with Topoisomerase I polypeptides or polynucleotides of the present invention, including, for example enzyme substrates, such as supercoiled DNA, cell membrane components and classical receptors. Binding between polypeptides of the invention and such molecules, including binding or interaction molecules may be exclusive to polypeptides of the invention, which is preferred, or it may be highly specific for polypeptides of the invention, which is also preferred, or it may be highly specific to a group of proteins that includes polypeptides of the invention, which is preferred, or it may be specific to several groups of proteins at least one of which includes a polypeptide of the invention. Binding molecules also include antibodies and antibody-derived reagents that bind specifically to polypeptides of the invention.

GENETIC ELEMENT generally means a polynucleotide comprising a region that encodes a polypeptide or a polynucleotide region that regulates replication, transcription or translation or other processes important to expression of the polypeptide in a host cell, or a polynucleotide comprising both a region that encodes a polypeptide and a region operably linked thereto that regulates expression. Genetic elements may be comprised within a vector that replicates as an episomal element; that is, as a molecule physically independent of the host cell genome. They may be comprised within plasmids. Genetic elements also may be comprised within a host cell genome; not in their natural state but, rather, following manipulation such as isolation, cloning and introduction into a host cell in the form of purified DNA or in a vector, among others.

HOST CELL is a cell which has been transformed or transfected, or is capable of transformation or transfection by an exogenous polynucleotide sequence.

IDENTITY as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data,* Part I, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991; and Carillo, H., and Lipman, D., SIAM *J. Applied Math.,* 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1):387 (1984)), BLASTP, BLASTN, and FASTA (Atschul, S. F. et al., *J. Molec. Biol.* 215: 403–410 (1990). The BLAST X program is publicly available from NCBI and other sources (*BLAST Manual,* Altschul, S., et al., NCBI NLM NIH Bethesda, Md. 20894; Altschul, S., et al., *J. Mol. Biol.* 215: 403–410 (1990). As an illustration, by a polynucleotide having a nucleotide sequence having at least, for example, 95% "identity" to a reference nucleotide sequence of SEQ ID NO:1 it is intended that the nucleotide sequence of the polynucleotide is identical to the reference sequence except that the polynucleotide sequence may include up to five point mutations per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO:2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

ISOLATED means altered "by the hand of man" from its natural state; i.e., that, if it occurs in nature, it has been changed or removed from its original environment, or both. For example, a naturally occurring polynucleotide or a polypeptide naturally present in a living organism in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs. As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

POLYNUCLEOTIDE(S) generally refers to any polyribonucleotide or polydeoxribonucleotide, which may be unmodified RNA or DNA or modified RNA or DNA. Thus, for instance, polynucleotides as used herein refers to, among others, single-and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells. The term polynucleotide(s) embrace short polynucleotides often referred as oligonucleotides.

POLYPEPTIDES, as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance PROTEINS— STRUCTURE AND MOLECULAR PROPERTIES, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York (1983); Seifter et al., Meth. Enzymol. 182:626–646 (1990) and Rattan et al., Protein Synthesis: Posttranslational Modifications and Aging, Ann. N.Y. Acad. Sci. 663: 48–62 (1992). It will be appreciated, as is well known and as noted above, that polypeptides are not always entirely linear. For instance, polypeptides may be branched as a result of ubiquitination, and they may be circular, with or without branching, generally as a result of posttranslational events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in E. coli or other cells, prior to proteolytic processing, almost invariably will be N-formylmethionine. During post-translational modification of the peptide, a methionine residue at the NH$_2$-terminus may be deleted. Accordingly, this invention contemplates the use of both the methionine-containing and the methionineless amino terminal variants of the protein of the invention. The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as, for example, E. coli. Accordingly, when glycosylation is desired, a polypeptide should be expressed in a glycosylating host, generally a eukaryotic cell. Insect cells often carry out the same posttranslational glycosylations as do mammalian cells and, for this reason, insect cell expression systems have been developed to express efficiently mammalian proteins having native patterns of glycosylation. Similar considerations apply to other modifications. It will be appreciated that the same type of modification may be present in the same or varying degree at several sites in a given polypeptide. Also, a given polypeptide may contain many types of modifications. In general, as used herein, the term polypeptide encompasses all such modifications, particularly those that are present in polypeptides synthesized by expressing a polynucleotide in a host cell.

VARIANT(S) of polynucleotides or polypeptides, as the term is used herein, are polynucleotides or polypeptides that differ from a reference polynucleotide or polypeptide, respectively. Variants in this sense are described below and elsewhere in the present disclosure in greater detail. With reference to polynucleotides, generally, differences are limited such that the nucleotide sequences of the reference and the variant are closely similar overall and, in many regions, identical. As noted below, changes in the nucleotide sequence of the variant may be silent. That is, they may not alter the amino acids encoded by the polynucleotide. Where alterations are limited to silent changes of this type, a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below. With reference to polypeptides generally, differences are limited so that the sequences of the reference and the variant are closely similar overall and, in many region, identical. A variant and reference polypeptide may differ in amino acid sequence by one or more substitutions, additions, deletions, fusions and truncations, which may be present in any combination.

DESCRIPTION OF THE INVENTION

The present invention relates to novel Topoisomerase I polypeptides and polynucleotides encoding same, among other things, as described in greater detail below. In particular, the invention relates to polypeptides and polynucleotides of a novel Topoisomerase I gene of Staphylococcus aureus, which is related by amino acid sequence homology to Bacillus subtilis topoisomerase I polypeptide. The invention relates especially to Staphylococcal Topoisomerase I having the nucleotide and amino acid sequences set out in FIG. 1 (SEQ ID NO:1) and FIG. 2 (SEQ ID NO:2) and FIG. 3, and to the Topoisomerase I nucleotide and amino acid sequences of the DNA isolatable from Deposit No. NC1MB 40771, which is herein referred to as "the deposited organism" or as the "DNA of the deposited organism." It will be appreciated that the nucleotide and amino acid sequences set out in FIG. 1 (SEQ ID NO:1) and FIG. 2 (SEQ ID NO:2) were obtained by sequencing the DNA of the deposited organism. Hence, the sequence of the deposited clone is controlling as to any discrepancies between it (and the sequence it encodes) and the sequences of FIG. 1 (SEQ ID NO:1) and FIG. 2 (SEQ ID NO:2).

Polynucleotides

In accordance with one aspect of the present invention, there are provided isolated polynucleotides which encode the Staphylococcal Topoisomerase I polypeptide having the deduced amino acid sequence of FIG. 2 (SEQ ID NO:2).

Using the information provided herein, such as the polynucleotide sequence set out in FIG. 1 (SEQ ID NO:1), a polynucleotide of the present invention encoding Topoisomerase I polypeptide may be obtained using standard cloning and screening procedures. To obtain the polynucleotide encoding the protein using the DNA sequence given in SEQ ID NO:1 typically a library of clones of chromosomal DNA of S. aureus WCUH 29 in E. coli or some other suitable host is probed with a radiolabelled oligonucleotide, preferably a 17mer or longer, derived from the sequence of FIG. 1. Clones carrying DNA identical to that of the probe can then be distinguished using high stringency washes. By sequencing the individual clones thus identified with sequencing primers designed from the original sequence it is then possible to extend the sequence in both directions to determine the full gene sequence. Conveniently such sequencing is performed using denatured double stranded DNA prepared from a plasmid clone. Suitable techniques are described by Maniatis, T., Fritsch, E. F. and Sambrook, J. in *MOLECULAR CLONING*, A Laboratory Manual (2nd edition 1989 Cold Spring Harbor Laboratory. see Screening By Hybridization 1.90 and Sequencing Denatured Double-Stranded DNA Templates 13.70). Illustrative of the invention, the polynucleotide set out in FIG. 1 (SEQ ID NO:1) was discovered in a DNA library derived from *Staphylococcus aureus* NC 1MB 40771 as described in Example I.

Topoisomerase I of the invention is structurally related to other proteins of the bacterial Topoisomerase I family, as shown by comparing the sequence encoding Topoisomerase I from the deposited clone with that of sequence reported in the literature. A preferred DNA sequence is set out in FIG. 1 ( SEQ ID NO:1. It contains an open reading frame encoding a protein of about 691 amino acid residues with a deduced molecular weight of about 79.292 kDa. The protein exhibits greatest homology to *Bacillus subtilis* topoisomerase I protein among known proteins. Topoisomerase I of FIG. 2 (SEQ ID NO:2) has about 68% identity and about 80% similarity with the amino acid sequence of *Bacillus subtilis* topoisomerase I.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The coding sequence which encodes the polypeptide may be identical to the coding sequence of the polynucleotide shown in FIG. 1 (SEQ ID NO:1). It also may be a polynucleotide with a different sequence, which, as a result of the redundancy (degeneracy) of the genetic code, encodes the polypeptide of FIG. 2 (SEQ ID NO:2). FIG. 3 illustrates all such coding sequences.

Polynucleotides of the present invention which encode the polypeptide of FIG. 2 (SEQ ID NO:2) may include, but are not limited to the coding sequence for the mature polypeptide, by itself; the coding sequence for the mature polypeptide and additional coding sequences, such as those encoding a leader or secretory sequence, such as a pre-, or pro- or prepro-protein sequence; the coding sequence of the mature polypeptide, with or without the aforementioned additional coding sequences, together with additional, non-coding sequences, including for example, but not limited to non-coding 5' and 3' sequences, such as the transcribed, non-translated sequences that play a role in transcription (including termination signals, for example), ribosome binding, mRNA stability elements, and additional coding sequence which encode additional amino acids, such as those which provide additional functionalities. The DNA may also comprise a promoter region which functions to direct the transcription of the mRNA encoding the Topoisomerase I of this invention. Such promoter may be independently useful to direct the transcription of heterologous gene in recombinant expression system. Furthermore, the polypeptide may be fused to a marker sequence, such as a peptide, which facilitates purification of the fused polypeptide. In certain embodiments of this aspect of the invention, the marker sequence is a hexa-histidine peptide, such as the tag provided in the pQE vector (Qiagen, Inc.), among others, many of which are commercially available. As described in Gentz et al., *Proc. Natl. Acad. Sci.*, USA 86: 821–824 (1989), for instance, hexa-histidine provides for convenient purification of the fusion protein. The HA tag may also be used to create fusion proteins and corresponds to an epitope derived of influenza hemagglutinin protein, which has been described by Wilson et al., *Cell* 37: 767 (1984), for instance.

In accordance with the foregoing, the term "polynucleotide encoding a polypeptide" as used herein encompasses polynucleotides which include a sequence encoding a polypeptide of the present invention, particularly bacterial, and more particularly *Staphylococcus aureus* Topoisomerase I having the amino acid sequence set out in FIG. 2 (SEQ ID NO:2). The term encompasses polynucleotides that include a single continuous region or discontinuous regions encoding the polypeptide (for example, interrupted by integrated phage or insertion sequence or editing) together with additional regions, that also may contain coding and/or non-coding sequences.

The invention also includes polynucleotides of the formula:

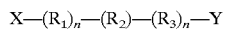

$$X—(R_1)_n—(R_2)—(R_3)_n—Y$$

wherein, at the 5' end of the molecule, X is hydrogen, and at the 3' end of the molecule, Y is hydrogen or a metal, $R_1$ and $R_3$ is any nucleic acid residue, n is an integer between 1 and 3000, and $R_2$ is a nucleic acid sequence of the invention, particularly the polynucleotide sequence of SEQ ID NO:1. In the polynucleotide formula above $R_2$ is oriented so that its 5' end residue is at the left, covalently bonded to $R_1$, and its 3' end residue is at the right, covalently bonded to $R_3$. Any stretch of nucleic acid residues denoted by either R group, where R is greater than 1, may be either a heteropolymer or a homopolymer, preferably a heteropolymer. In a preferred embodiment n is an integer between 1 and 1000.

The present invention further relates to variants of the herein above described polynucleotides which encode for fragments, analogs and derivatives of the polypeptide having the deduced amino acid sequence of FIG. 2 (SEQ ID NO:2). A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence of Staphylococcal Topoisomerase I set out in FIG. 2 (SEQ ID NO:2); variants, analogs, derivatives and fragments thereof.

Further particularly preferred in this regard are polynucleotides encoding Topoisomerase I variants, analogs, derivatives and fragments, and variants, analogs and derivatives of the fragments, which have the amino acid sequence of Staphylococcal Topoisomerase I polypeptide of FIG. 2 (SEQ ID NO:2) in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of Topoisomerase I. Also especially preferred in this regard are conservative substitutions. Most highly preferred are polynucleotides encoding polypeptides having the amino acid sequence of FIG. 2 (SEQ ID NO:2), without substitutions.

Further preferred embodiments of the invention are polynucleotides that are at least 70% identical to a polynucleotide encoding Topoisomerase I polypeptide having the amino acid sequence set out in FIG. 2 (SEQ ID NO:2), and polynucleotides which are complementary to such polynucleotides. Alternatively, most highly preferred are polynucleotides that comprise a region that is at least 80% identical to a polynucleotide encoding Topoisomerase I polypeptide of the *Staphylococcus aureus* DNA of the deposited clone and polynucleotides complementary thereto. In this regard, polynucleotides at least 90% identical to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Particularly preferred embodiments in this respect, moreover, are polynucleotides which encode polypeptides which retain substantially the same biological function or activity as the mature polypeptide encoded by the DNA of FIG. 1 (SEQ ID NO:1).

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences. An example of stringent hybridization conditions is overnight incubation at 42° C. in a solution comprising:50% formamide, 5× SSC (150 mM NaCl, 15 mM trisodium citrate), 50 mM sodium phosphate (pH7.6), 5× Denhardt's solution, 10% dextran sulfate, and 20 micrograms/ml denatured, sheared salmon sperm DNA, followed by washing the hybridization support in 0.1× SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein.

As discussed additionally herein regarding polynucleotide assays of the invention, for instance, polynucleotides of the invention as discussed above, may be used as a hybridization probe for RNA, cDNA and genomic DNA to isolate full-length cDNAs and genomic clones encoding Topoisomerase I and to isolate cDNA and genomic clones of other genes that have a high sequence similarity to the Topoisomerase I gene. Such probes generally will comprise at least 15 bases. Preferably, such probes will have at least 30 bases and may have at least 50 bases. Particularly preferred probes will have at least 30 bases and will have 50 bases or less.

For example, the coding region of the Topoisomerase I gene may be isolated by screening using the known DNA sequence to synthesize an oligonucleotide probe. A labeled oligonucleotide having a sequence complementary to that of a gene of the present invention is then used to screen a library of cDNA, genomic DNA or mRNA to determine which members of the library to which the probe hybridizes.

The polynucleotides and polypeptides of the present invention may be employed as research reagents and materials for discovery of treatments of and diagnostics for disease, particularly human disease, as further discussed herein relating to polynucleotide assays.

The polynucleotides of the invention that are oligonucleotides, derived from the sequences (SEQ ID NO:1) may be used as PCR primers in the process herein described to determine whether or not the *Staphylococcus aureus* genes identified herein in whole or in part are transcribed in infected tissue. It is recognized that such sequences will also have utility in diagnosis of the stage of infection and type of infection the pathogen has attained.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case, in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Deposited Materials

*Staphylococcus aureus* WCUH 29 was deposited at the National Collection of Industrial and Marine Bacteria Ltd. (NCIMB), Aberdeen, Scotland under number NCIMB 40771 on Sep. 11, 1995.

The deposit has been made under the terms of the Budapest Treaty on the International Recognition of the Deposit of Micro-organisms for Purposes of Patent Procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. §112.

The sequence of the polynucleotides contained in the deposited material, as well as the amino acid sequence of the polypeptide encoded thereby, are controlling in the event of any conflict with any description of sequences herein.

A license may be required to make, use or sell the deposited materials, and no such license is hereby granted.

Polypeptides

The present invention further relates to a bacterial Topoisomerase I polypeptide that has the deduced amino acid sequence of FIG. 2 (SEQ ID NO:2).

The invention also relates to fragments, analogs and derivatives of these polypeptides. The terms "fragment," "derivative" and "analog" when referring to the polypeptide of FIG. 2 (SEQ ID NO:2), means a polypeptide which retains essentially the same biological function or activity as such polypeptide. Fragments derivatives and analogs that retain at least 90% of the activity of the native Topoisomerase I are preferred. . Fragments derivatives and analogs that retain at least 95% of the activity of the native Topoisomerase I are preferred Thus, an analog includes a proprotein which can be activated by cleavage of the proprotein portion to produce an active mature polypeptide.

The polypeptide of the present invention may be a recombinant polypeptide, a natural polypeptide or a synthetic polypeptide. In certain preferred embodiments it is a recombinant polypeptide.

The fragment, derivative or analog of the polypeptide of FIG. 2 (SEQ ID NO:2) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be obtained by those of ordinary skill in the art, from the teachings herein.

The invention also includes polypeptides of the formula:

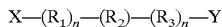

$$X-(R_1)_n-(R_2)-(R_3)_n-Y$$

wherein, at the amino terminus, X is hydrogen, and at the carboxyl terminus, Y is hydrogen or a metal, $R_1$ and $R_3$ are any amino acid residue, n is an integer between 1 and 1000, and $R_2$ is an amino acid sequence of the invention, particularly the polypeptide of SEQ ID NO:2. In the formula above $R_2$ is oriented so that its amino terminal residue is at the left, covalently bonded via a peptide linkage to $R_1$, and its carboxy terminal residue is at the right, covalently bonded via a peptide linkage to $R_3$. Any stretch of amino acid residues denoted by either R group, where R is greater than 1, may be either a heteropolymer or a homopolymer, preferably a heteropolymer.

Among the particularly preferred embodiments of the invention in this regard are polypeptides having the amino acid sequence of Staphylococcal Topoisomerase I set out in FIG. 2 (SEQ ID NO:2), variants, analogs, derivatives and fragments thereof, and variants, analogs and derivatives of the fragments.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Further particularly preferred in this regard are variants, analogs, derivatives and fragments, and variants, analogs and derivatives of the fragments, having the amino acid sequence of the Topoisomerase I polypeptide of FIG. 2 (SEQ ID NO:2), in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the Topoisomerase I. Also especially preferred in this regard are conservative substitutions. Most highly preferred are polypeptides having the amino acid sequence of FIG. 2 (SEQ ID NO:2) without substitutions.

The polypeptides and polynucleotides of the present invention are preferably provided in an isolated form, and preferably are purified to homogeneity.

The polypeptides of the present invention include the polypeptide of FIG. 2 (SEQ ID NO:2), in particular the mature polypeptide as well as polypeptides which have at least 80% identity to the polypeptide of FIG. 2 (SEQ ID NO:2) and preferably at least 90% similarity (more preferably at least 90% identity) to the polypeptide of FIG. 2 (SEQ ID NO:2) and more preferably at least 95% similarity; and still more preferably at least 95% identity to the polypeptide of FIG. 2 (SEQ ID NO:2) and also include portions of such polypeptides with such portion of the polypeptide generally containing at least 30 contiguous amino acids and more preferably at least 50 contiguous amino acids.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

Fragments

Also among preferred embodiments of this aspect of the present invention are polypeptides comprising fragments of Topoisomerase L most particularly fragments of Topoisomerase I having the amino acid set out in FIG. 2 (SEQ ID NO:2), and fragments of variants and derivatives of the Topoisomerase I of FIG. 2 (SEQ ID NO:2).

In this regard a fragment is a polypeptide having an amino acid sequence that entirely is the same as part but not all of the amino acid sequence of the aforementioned Topoisomerase I polypeptides and variants or derivatives thereof.

Such fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a Topoisomerase I polypeptide of the present comprised within a precursor polypeptide designed for expression in a host and having beterologous pre and pro-polypeptide regions fused to the amino terminus of the Topoisomerase I fragment and an additional region fused to the carboxyl terminus of the fragment. Therefore, fragments in one aspect of the meaning intended herein, refers to the portion or portions of a fusion polypeptide or fusion protein derived from Topoisomerase I.

Representative examples of polypeptide fragments of the invention, include, for example, may be mentioned those which have from about 5–15, 10–20, 15–40, 30–55, 41–75, 41–80, 41–90, 50–100, 75–100, 90–115, 100–125, and 110–140, 120–150, 200–300, 1–175 or 1–600 amino acids long. Particular examples of polypeptide fragments of the inventions that may be mentioned include fragments from amino acid number 1–173, 1–574 and 193–451.

In this context about includes the particularly recited range and ranges larger or smaller by several, a few, 5, 4, 3, 2 or 1 amino acid at either extreme or at both extremes.

Among especially preferred fragments of the invention are truncation mutants of Topoisomerase I. Truncation mutants include Topoisomerase I polypeptides having the amino acid sequence of FIG. 2 (SEQ ID NO:2), or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out above also are preferred embodiments of truncation fragments, which are especially preferred among fragments generally. Degradation forms of the polypeptides of the invention in a host cell are also preferred.

Also preferred in this aspect of the invention are fragments characterized by structural or functional attributes of Topoisomerase I. Preferred embodiments of the invention in this regard include fragments that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of Topoisomerase I.

Further preferred regions are those that mediate activities of Topoisomerase I. Most highly preferred in this regard are fragments that have a chemical, biological or other activity of Topoisomerase I, including those with a similar activity or an improved activity, or with a decreased undesirable activity. Routinely one generates the fragment by well-known methods then compares the activity of the fragment to nature Topoismerase I in a convenient assay such as listed hereinbelow. Highly preferred in this regard are fragments that contain regions that are homologs in sequence, or in position, or in both sequence and to active regions of related polypeptides, such as the related polypeptides set out in FIG. 2 (SEQ ID NO:2), which include *Bacillus subtilis* topoisomerase I and *E. coli* topoisomerase I. Among particularly preferred fragments in these regards are truncation mutants, as discussed above. Further preferred polynucleotide fragments are those that are antigenic or immunogenic in an animal, especially in a human.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspondent to the preferred fragments, as discussed above.

Vectors, Host Cells, Expression

The present invention also relates to vectors which comprise a polynucleotide or polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. Introduction of a polynucleotides into the host cell can be affected by calcium phosphate transfection, DEAE-dextran mediated transfection, transvection, microinjection, cationic lipid-mediated transfection, electroporation, transduction, scrape loading, ballistic introduction, infection or other methods. Such methods are described in many standard laboratory manuals, such as Davis et al., *BASIC METHODS IN MOLECULAR BIOLOGY*, (1986) and Sambrook et al, *MOLECULAR CLONING: A LABORATORY MANUAL*, 2nd Ed., Cold Spring Harbor Laboratory Press, Cold Spring Harbor, N.Y. (1989).

Polynucleotide constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *MOLECULAR CLONING: A LABORATORY MANUAL*, 2nd Ed., Cold Spring Harbor Laboratory Press, Cold Spring Harbor, N.Y. (1989).

In accordance with this aspect of the invention the vector may be, for example, a plasmid vector, a single or double-stranded phage vector, a single or double-stranded RNA or DNA viral vector. Plasmids generally are designated herein by a lower case p preceded and/or followed by capital letters and/or numbers, in accordance with standard naming conventions that are familiar to those of skill in the art. Starting plasmids disclosed herein are either commercially available, publicly available, or can be constructed from available plasmids by routine application of well known, published procedures. Many plasmids and other cloning and expression vectors that can be used in accordance with the present invention are well known and readily available to those of skill in the art.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

A great variety of expression vectors can be used to express a polypeptide of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques, such as, for example, those set forth in Sambrook et al *MOLECULAR CLONING, A LABORATORY MANUAL,* 2nd Ed.; Cold Spring Harbor Laboratory Press, Cold Spring Harbor, N.Y. (1989).

The DNA sequence in the expression vector is operatively linked to appropriate expression control sequence(s), including, for instance, a promoter to direct mRNA transcription. Representatives of such promoters include, but are not limited to, the phage lambda PL promoter, the E coli lac, trp and tac promoters, the SV40 early and late promoters and promoters of retroviral LTRs.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as transcription factors, repressor binding sites and termination, among others.

Vectors for propagation and expression generally will include selectable markers and amplification regions, such as, for example, those set forth in Sambrook et al., *MOLECULAR CLONING, A LABORATORY MANUAL,* 2nd Ed.; Cold Spring Harbor Laboratory Press, Cold Spring Harbor, N.Y. (1989).

Representative examples of appropriate hosts include bacterial cells, such as streptococci, staphylococci, *E. coli,* streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223–3, pKK233–3, pDR540, pRIT5 available from Pharmacia, and pBR322 (ATCC 37017). Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available, such as pKK232-8 and pCM7. Promoters for expression of polynucleotides of the present invention include not only well known and readily available promoters, but also promoters that readily may be obtained by the foregoing technique, using a reporter gene.

Among known prokaryotic promoters suitable for expression of polynucleotides and polypeptides in accordance with the present invention are the *E. coli* lacI and lacZ and promoters, the T3 and T7 promoters, the gpt promoter, the lambda PR, PL promoters and the trp promoter.

Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Recombinant expression vectors will include, for example, origins of replication, a promoter preferably derived from a highly-expressed gene to direct transcription of a downstream structural sequence, and a selectable marker to permit isolation of vector containing cells after exposure to the vector.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiation codon. Also, generally, there will be a translation stop codon at the end of the polypeptide and there will be a polyadenylation signal in constructs for use in eukaryotic hosts. Transcription termination signal appropriately disposed at the 3' end of the transcribed region may also be included in the polynucleotide construct.

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N-or C-terminus of the polypeptide to improve stability and persistence in the host cell, during purification or during subsequent handling and storage. Also, region also may be added to the polypeptide to facilitate purification. Such regions may be removed prior to final preparation of the polypeptide. The addition of peptide moieties to polypeptides to engender secretion or excretion, to improve stability or to facilitate purification, among others, are familiar and routine techniques in the art. A preferred fusion protein comprises a heterologous region from immunogloblin that is useful to solubilize or purify polypeptides. For example, EP-A-O 464 533 (Canadian counterpart 2045869) discloses fusion proteins comprising various portions of constant region of immunoglobulin molecules together with another protein or part thereof. In drug discovery, for example, proteins have been fused with antibody Fc portions for the purpose of high-throughput screening assays to identify antagonists. See, D. Bennett et al, Journal of Molecular Recognition, 8: 52–58 (1995) and K. Johanson et al., The Journal of Biological Chemistry, 270,(16):9459–9471 (1995).

Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Mammalian expression vectors may comprise an origin of replication, a suitable promoter and enhancer, and also any necessary ribosome binding sites, polyadenylation sites, splice donor and acceptor sites, transcriptional termination sequences, and 5' flanking non-transcribed sequences that are necessary for expression. In certain preferred embodiments in this regard DNA sequences derived from the SV40 splice sites, and the SV40 polyadenylation sites are used for required non-transcribed genetic elements of these types.

Topoisomerase I polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and or purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Topoisomerase I polynucleotides and polypeptides may be used in accordance with the present invention for a variety of applications, particularly those that make use of the chemical and biological properties of Topoisomerase I. Additional applications relate to diagnosis and to treatment of disorders of cells, tissues and organisms. These aspects of the invention are illustrated further by the following discussion.

Polynucleotide Assays

This invention is also related to the use of the Topoisomerase I polynucleotides to detect complementary polynucleotides such as, for example, as a diagnostic reagent. Detection of a bacterial Topoisomerase I in a eukaryote, particularly a mammal, and especially a human, will provide a diagnostic method that can add to, define or allow a diagnosis of a disease. Eukaryotes (herein also "individual (s)"), particularly mammals, and especially humans, infected by a Topoisomerase I producing bacterium may be detected at the DNA or RNA level by a variety of techniques. Nucleic acids for diagnosis may be obtained from an individual's cells and tissues, such as bone, blood, muscle, cartilage, and skin. Tissue biopsy and autopsy material is also preferred for samples from an individual to use in a diagnostic assay. The bacterial DNA may be used directly for detection or may be amplified enzymatically by using PCR prior to analysis. PCR (Saiki et al., Nature 324: 163–166 (1986)). RNA or cDNA may also be used in the same ways. As an example, PCR primers complementary to the nucleic acid encoding Topoisomerase I can be used to identify and analyze Topoisomerase I presence and expression. Using PCR, characterization of the strain of prokaryote present in a eukaryote, particularly a mammal, and especially a human, may be made by an analysis of the genotype of the prokaryote gene. For example, deletions and insertions can be detected by a change in size of the amplified product in comparison to the genotype of a reference sequence. Point mutations can be identified by hybridizing amplified DNA to radiolabeled Topoisomerase I RNA or alternatively, radiolabeled Topoisomerase I antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic typing of various strains of bacteria based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al, Science, 230: 1242 (1985)).

Sequence changes at specific locations also may be revealed by nuclease protection assays, such as RNase and S1 protection or the chemical cleavage method (e.g., Cotton et Proc. Nat'l. Acad. Sci., USA, 85:43974401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In addition to more conventional gel-electrophoresis and DNA sequencing, mutations also can be detected by in situ analysis.

Cells carrying mutations or polymorphisms in the gene of the present invention may also be detected at the DNA level by a variety of techniques, to allow for serotyping, for example. Nucleic acids for diagnosis may be obtained from an infected individual's cells, including but not limited to blood, urine, saliva, tissue biopsy and autopsy material or from bacteria isolated and cultutered from the above sources. The bacterial DNA may be used directly for detection or may be amplified enzymatically by using PCR (Saiki et al., Nature, 324:163–166 (1986)) prior to analysis. RT-PCR can also be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to the nucleic acid encoding Topoisomerase I can be used to identify and analyze mutations. Examples of representative primers are shown below in Table 1. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

TABLE 1

Primers used for detection of mutations or polymorphisms in Topoisomerase I gene

| | SEQ ID NO: |
|---|---|
| 5'-GGGGAAATGACATTGGCAGATA-3' | 3 |
| 5'-TCTTAAAATGTCTCTAGGGAATAA-3' | 4 |

The above primers may be used for amplifying Topoisomerase I cDNA isolated from a sample derived from an individual. The invention also provides the primers of Table 1 with 1, 2, 3 or 4 nucleotides removed from the 5' and/or the 3' end. The primers may be used to amplify the gene isolated from the individual such that the gene may then be subject to various techniques for elucidation of the DNA sequence. In this way, mutations in the DNA sequence may be detected.

Polypeptide Assays

The present invention also relates to a diagnostic assays such as quantitative and diagnostic assays for detecting levels of Topoisomerase I protein in cells and tissues, including determination of normal and abnormal levels. Thus, for instance, a diagnostic assay in accordance with the invention for detecting expression of Topoisomerase I protein compared to normal control tissue samples may be used to detect the presence of an infection. Assay techniques that can be used to determine levels of a protein, such as an Topoisomerase I protein of the present invention, in a sample derived from a host are well-known to those of skill in the art. Such assay methods include radioimmunoassays, competitive-binding assays, Western Blot analysis and ELISA assays. Among these ELISAs frequently are preferred. An ELISA assay initially comprises preparing an antibody specific to Topoisomerase I, preferably a monoclonal antibody. In addition a reporter antibody generally is prepared which binds to the monoclonal antibody. The reporter antibody is attached a detectable reagent such as radioactive, fluorescent or enzymatic reagent, in this example horseradish peroxidase enzyme.

Antibodies

The polypeptides, their fragments or other derivatives, or analogs thereof, or cells expressing them can be used as an immunogen to produce antibodies thereto. The present invention includes, for examples monoclonal and polyclonal antibodies, chimeric, single chain, and humanized antibodies, as well as Fab fragments, or the product of an Fab expression library.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique known in the art which provides antibodies produced by continuous cell line cultures can be used. Examples include various techniques, such as those in Kohler, G. and Milstein, C., *Nature* 256: 495–497 (1975); Kozbor et al., *Immunology Today* 4: 72 (1983); Cole et al., pg. 77–96 in *MONOCLONAL ANTIBODIES AND CANCER THERAPY*, Alan R. Liss, Inc. (1985).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

Alternatively phage display technology could be utilized to select antibody genes with binding activities towards the polypeptide either from repertoires of PCR amplified v-genes of lymphocytes from humans screened for possessing anti-topoisomerase I activity or from naive libraries (McCafferty, J. et al.,, Nature 348, 552–554 (1990); Marks, J. et al., *Biotechnology* 10: 779–783 (1992). The affinity of these antibodies can also be improved by chain shuffling (Clackson, T. et al., *Nature* 352, 624–628 (1991).

If two antigen binding domains are present each domain may be directed against a different epitope—termed 'bispecific' antibodies.

The above-described antibodies may be employed to isolate or to identify clones expressing the polypeptide or purify the polypeptide of the present invention by attachment of the antibody to a solid support for isolation and/or purification by affinity chromatography. Thus among others, antibodies against Topoisomerase I may be employed to inhibit and/or treat infections, particularly bacterial infections, and especially Staphylococcal infections as well as to monitor the effectiveness of antibiotic treatment.

Polypeptide derivatives include antigenically, epitopically or immunologically equivalent derivatives which form a particular aspect of this invention. The term "antigenically equivalent derivative" as used herein encompasses a polypeptide or its equivalent which will be specifically recognized by certain antibodies which, when raised to the protein or polypeptide according to the present invention, interfere with the immediate physical interaction between pathogen and mammalian host. The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof may be sufficiently antigenic to improve immunogenicity so as to obviate the use of a carrier.

Preferably the antibody or derivative thereof is modified to make it less immunogenic in the individual. For example, if the individual is human the antibody may most preferably be "humanised"; where the complimentarily determining region(s) of the hybridoma-derived antibody has been transplanted into a human monoclonal antibody, for example as described in Jones, P. et al. Nature 321: 522–525 (1986)or Tempest et al., Biotechnology 9: 266–273 (1991).

The use of a polynucleotide of the invention in genetic immunization will preferably employ a suitable delivery method such as direct injection of plasmid DNA into muscles (Wolff et al., Hum Mol Genet 1:363 (1992), Manthorpe et al Hum. Gene Ther. 1963:4: 419 (1963), delivery of DNA complexed with specific protein carriers (Wu et al., J. Biol. Chem. 264:16985 (1989), coprecipitation of DNA with calcium phosphate (Benvenisty and Reshef, Proc. Nat'l Acad. Sci. (USA),:83;9551 (1986), encapsulation of DNA in various forms of liposomes (Kaneda et al., Science 243:375 (1989), particle bombardment (Tang et al., Nature, (1992) 356:152, Eisenbraun et al., DNA Cell Biol 12:791(1993) and in vivo infection using cloned retroviral vectors (Seeger et al., Proc. Nat'l Acad. Sci. (USA) 81:5849 (1984).

Topoisomerase I Binding Molecules and Assays

This invention also provides a method for identification of molecules, such as binding molecules, that bind Topoisomerase I. Genes encoding proteins that bind Topoisomerase I, such as binding proteins, can be identified by numerous methods known to those of skill in the art, for example, ligand panning and FACS sorting. Such methods are described in many laboratory manuals such as, for instance, Coligan et al., Current Protocols in Immunology 1(2): Chapter 5 (1991).

For instance, expression cloning may be employed for this purpose. To this end polyadenylated RNA is prepared from a cell expressing Topoisomerase I, a cDNA library is created from this RNA, the library is divided into pools and the pools are transfected individually into cells that are not expressing to Topoisomerase I. The transfected cells then are exposed to labeled Topoisomerase I. Topoisomerase I can be labeled by a variety of well-known techniques including standard methods of radio-iodination or inclusion of a recognition site for a site-specific protein kinase.) Following exposure, the cells are fixed and binding of Topoisomerase I is determined. These procedures conveniently are carried out on glass slides.

Pools are identified of cDNA that produced Topoisomerase I-binding cells. Sub-pools are prepared from these positives, transfected into host cells and screened as described above. Using an iterative sub-pooling and re-screening process, one or more single clones that encode the putative binding molecule, such as a binding molecule, can be isolated.

Alternatively a labeled ligand can be photoaffinity linked to a cell extract, such as a membrane or a membrane extract, prepared from cells that express a molecule that it binds, such as a binding molecule. Cross4inked material is resolved by polyacrylamide gel electrophoresis ("PAGE") and exposed to X-ray film. The labeled complex containing the ligand-binding can be excised, resolved into peptide fragments, and subjected to protein microsequencing. The amino acid sequence obtained from microsequencing can be used to design unique or degenerate oligonucleotide probes to screen cDNA libraries to identify genes encoding the putative binding molecule.

Polypeptides of the invention also can be used to assess Topoisomerase I binding capacity of Topoisomerase I binding molecules, such as binding molecules, in cells or in cell-free preparations.

Polypeptides of the invention may also be used to assess the binding or small molecule substrates and ligands in, for example, cells, cell-free preparations, chemical libraries, and natural product mixtures. These substrates and ligands may be natural substrates and ligands or may be structural or functional mimetics.

Antagonists and Agonists—Assays and Molecules

As mentioned above, both increases and decreases in DNA density have been associated with bacterial responses to environmental challenges. Accordingly, modulating, i.e., agonizing or antagonizing, the appropriate response could result in a potential antibiotic effect.

The invention also provides a method of screening compounds to identify those which enhance or block the action of Topoisomerase I on cells, such as its interaction with substrate molecules, such as supercoiled DNA. Compounds which block the action of Topoisomerase I on cells include those which act as poisons and stabilize Topoisomerase I in a covalent complex with DNA, resulting in an inhibitory effect on cell growth. An antagonist is a compound which decreases the natural biological functions of Topoisomerase I. An agonist is a compound which increases the natural biological functions of Topoisomerase I.

Barrett et al, Antimicrob. Agents Chemother. 34:1 (1990) review in-vitro assays which can be used to measure inhibition of topoisomerases. These assays can be categorized as catalytic assays and noncatalytic assays. Catalytic assays for bacterial topoisomerase I include, for example, assays to measure the relaxation of supercoiled DNA. Noncatalytic assays, also known as 'cleavable complex' assays, measure the formation of a key covalent reaction intermediate. Froelich-Ammon and Osheroff J. Biol. Chem. 270:21429 (1995) review the mechanistic basis of noncatalytic assays of topoisomerase poisons.

Supercoiled DNA Relaxation Assay

To screen for inhibitors of the relaxation reaction, a candidate inhibitor and a preparation of Topoisomerase I are incubated with a supercoiled DNA substrate, for example plasmid or phage DNA, in an appropriate buffer containing $Mg^{2+}$, or an alternative divalent metal ion. Reaction products are separated by agarose gel electrophoresis, visualized by ethidium bromide staining, and quantified by densitometry.

DNA Oligomer Cleavage Assay

A single stranded DNA oligomer containing appropriate sites, for example the 22mer GAATGAGCCGCAACT- TCGGGAT (SEQ ID NO:7), or an appropriately labelled derivative, may be used as substrate. An appropriate label may be a radiolabel or a fluorescent chromophore attached at the 5' or 3' end of the oligo, according to the specific assay used. The substrate is incubated with a candidate inhibitor and a preparation of Topoisomerase I, in an appropriate buffer. The buffer may contain $Mg^{2+}$ or an alternative divalent metal ion. $Mg^{2+}$ is not essential for the cleavage reaction, although its inclusion may be desirable to facilitate the interaction of certain classes of inhibitors. The reaction is stopped by the addition of an appropriate denaturant, for example 1% SDS or 100 mM NaOH. Generation of the cleavable complex (stabilization of the key covalent reaction intermediate) may be measured by a number of methods. For example, electrophoresis using a denaturing polyacrylamide gel can be used to separate the 5' labelled cleaved DNA product which may then be quantified by densitometry. Alternatively, the 3' labelled DNA product may be assayed by virtue of its covalent association with Topoisomerase I. This may be performed by the SDS/K precipitation assay, in which radiolabelled DNA associated with precipitated protein is measured, or by a capture assay format in which Topoisomerase I is immobilized using an antibody and the amount of associated labelled DNA is measured.

Whole Cell Assays

Topoisomerase I-like effects of potential agonists and antagonists and poisons, may by measured, for instance, by determining activity of a reporter system that is sensitive to alterations in gene expression following interaction of the candidate molecule with a cell or appropriate cell preparation. Reporter systems that may be useful in this regard include but are not limited to colorimetric labeled substrate converted into product, a reporter gene that is responsive to changes in Topoisomerase I activity, and binding assays known in the art.

Potential antagonists include small organic molecules, peptides, polypeptides and antibodies that bind to a polypeptide of the invention and thereby inhibit or extinguish its activity, or stabilize the key covalent reaction intermediate with DNA. Potential antagonists also may be small organic molecules, a peptide, a polypeptide such as a closely related protein or antibody that binds the same sites on a binding molecule, such as a binding molecule, without inducing Topoisomerase I-induced activities, thereby preventing the action of Topoisomerase I by excluding Topoisomerase I from binding.

Potential antagonists include a small molecule which binds to and occupies the binding site of the polypeptide thereby preventing binding to cellular binding molecules, such as binding molecules, such that normal biological activity is prevented. Examples of small molecules include but are not limited to small organic molecules, peptides or peptide-like molecules.

Other potential antagonists include antisense molecules. Antisense technology can be used to control gene expression through antisense DNA or RNA or through double- or triple-helix formation. Antisense techniques are discussed, for example, in—Okano, J. Neurochem. 56: 560 (1991); *OLIGODEOXYNUCLEOTIDES AS ANTISENSE INHIBITORS OF GENE EXPRESSION*, CRC Press, Boca Raton, Fla. (1988). Triple helix formation is discussed in, for instance Lee et al., *Nucleic Acids Research* 6: 3073 (1979); Cooney et al., *Science* 241: 456 (1988); and Dervan et al., *Science* 251: 1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of Topoisomerase I. The antisense RNA oligonucleotide hybridizes to the mRNA in vivo and blocks translation of the mRNA molecule into Topoisomerase I polypeptide. The oligonucleotides described above can also be delivered to cells such that the antisense RNA or DNA may be expressed in vivo to inhibit production of Topoisomerase I.

Preferred potential antagonists include compounds related to and derivatives of each of the DNA sequences provided herein may be used in the discovery and development of antibacterial compounds. The encoded protein upon expression can be used as a target for the screening of antibacterial drugs. Additionally, the DNA sequences encoding the amino terminal regions of the encoded protein or Shine-Delgarno or other translation facilitating sequences of the respective mRNA can be used to construct antisense sequences to control the expression of the coding sequence of interest.

The antagonists and agonists of the invention may be employed in a composition with a pharmaceutically acceptable carrier, e.g., as hereinafter described.

The antagonists and agonists may be employed for instance to inhibit staphylococcal infections.

Vaccines

Another aspect of the invention relates to a method for inducing an immunological response in an individual, particularly a mammal which comprises inoculating the individual with Topoisomerase I, or a antigenic fragment or variant thereof, adequate to produce antibody to protect said individual from infection, particularly bacterial infection and most particularly Staphylococcal infection. Yet another aspect of the invention relates to a method of inducing immunological response in an individual which comprises, through gene therapy, delivering gene encoding Topoisomerase I, or a antigenic fragment or a variant thereof, for expressing Topoisomerase I, or a fragment or a variant thereof in vivo in order to induce an immunological response to produce antibody to protect said individual from disease.

A further aspect of the invention relates to an immunological composition which, when introduced into a host capable or having induced within it an immunological response, induces an immunological response in such host to a Topoisomerase I or protein coded therefrom, wherein the composition comprises a recombinant Topoisomerase I or protein coded therefrom comprising DNA which codes for and expresses an antigen of said Topoisomerase I or protein coded therefrom.

The Topoisomerase I or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as Glutathione-S-transferase (GSI) or beta-galactosidase, relatively large co-proteins which solubilise the protein and facilitate production and purification thereof. Moreover, the co-protein may act as an adjuvant in the sense of providing a generalized stimulation of the immune system. The co-protein may be attached to either the amino or carboxy terminus of the first protein.

The present invention also includes a vaccine formulation which comprises the immunogenic recombinant protein together with a suitable carrier. Since the protein may be broken down in the stomach, it is preferably administered parenterally, including, for example, administration that is subcutaneous, intramuscular, intravenous, or intradermal.

Formulations suitable for parenteral administration include aqueous and non-aqueous sterile injection solutions which may contain anti-oxidants, buffers, bacteriostats and solutes which render the formulation instonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Whilst the invention has been described with reference to certain Topoisomerase I, it is to be understood that this covers fragments of the naturally occurring protein and similar proteins (for example, having sequence homologies of 50% or greater) with additions, deletions or substitutions which do not substantially affect the immunogenic properties of the recombinant protein.

Compositions

The invention also relates to compositions comprising the polynucleotide or the polypeptides discussed above or the agonists or antagonists. Thus, the polypeptides of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

Kits

The invention further relates to diagnostic and pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Administration

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 $\mu$g/kg body weight. In most cases they will be administered in an amount not in excess of about 8 mg/kg body weight per day. Preferably, in most cases, dose is from about 10 p/kg to about 1 mg/kg body weight, daily. It will be appreciated that optimum dosage will be determined by standard methods for each treatment modality and indication, taking into account the indication, its severity, route of administration, complicating conditions and the like.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters, etc.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent Staphylococcal wound infections.

Many orthopedic surgeons consider that humans with prosthetic joints should be considered for antibiotic prophylaxis before dental treatment that could produce a bacteraemia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 1 µg/ml to 10 mg/ml for bathing of wounds or indwelling devices.

A vaccine composition is conveniently in injectable form. Conventional adjuvants may be employed to enhance the immune response.

A suitable unit dose for vaccination is 0.5–5 microgram/kg of antigen, and such dose is preferably administered 1–3 times and with an interval of 1–3 weeks.

With the indicated dose range, no adverse toxicological effects will be observed with the compounds of the invention which would preclude their administration to suitable individuals.

The antibodies described above may also be used as diagnostic reagents to detect the presence of bacteria containing Topoisomerase.

Each reference disclosed herein is incorporated by reference herein in its entirety. Any patent application to which this application claims priority is also incorporated by reference herein in its entirety.

In order to facilitate understanding of the following example certain frequently occurring methods and/or terms will be described.

EXAMPLES

The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

Certain terms used herein are explained in the foregoing glossary.

All examples were carried out using standard techniques, which are well known and routine to those of skill in the art, except where otherwise described in detail. Routine molecular biology techniques of the following examples can be carried out as described in standard laboratory manuals, such as Sambrook et al., *MOLECULAR CLONING: A LABORATORY MANUAL*, 2nd Ed.; Cold Spring Harbor Laboratory Press, Cold Spring Harbor, N.Y. (1989).

All parts or amounts set out in the following examples are by weight, unless otherwise specified.

Unless otherwise stated size separation of fragments in the examples below was carried out using standard techniques of agarose and polyacrylamide gel electrophoresis ("PAGE") in Sambrook et al., *MOLECULAR CLONING: A LABORATORY MANUAL*, 2nd Ed., Cold Spring Harbor Laboratory Press, Cold Spring Harbor, N.Y. (1989) and numerous other references such as, for instance, by Goeddel et al., *Nucleic Acids Res.* 8: 4057 (1980).

Unless described otherwise, ligations were accomplished using standard buffers, incubation temperatures and times, approximately equimolar amounts of the DNA fragments to be ligated and approximately 10 units of T4 DNA ligase ("ligase") per 0.5 microgram of DNA.

The polynucleotide having the DNA sequence given in (SEQ ID NO:1) was obtained from the sequencing of a library of clones of chromosomal DNA of *Staphylococcus aureus* WCUH 29 in *E. coli*.

To obtain the polynucleotide encoding the Topoisomerase I protein using the DNA sequence given in (SEQ ID NO:1) typically a library of clones of chromosomal DNA of *Staphylococcus aureus* WCUH 29 in *E. coli* or some other suitable host is probed with a radiolabelled oligonucleotide, preferably a 17mer or longer, derived from the partial sequence. Clones carrying DNA identical to that of the probe can then be distinguished using high stringency washes. By sequencing the individual clones thus identified with sequencing primers designed from the original sequence it is then possible to extend the sequence in both directions to determine the full gene sequence. Conveniently such sequencing is performed using denatured double stranded DNA prepared from a plasmid clone. Suitable techniques are described by Maniatis, T., Fritsch, E. F. and Sambrook et al. *MOLECULAR CLONING, A LABORATORY MANUAL*, 2nd Ed.; Cold Spring Harbor Laboratory Press, Cold Spring Harbor, N.Y. (1989). (see Screening By Hybridization 1.90 and Sequencing Denatured Double-Stranded DNA Templates 13.70).

Example 1

Isolation of DNA Coding for Novel Topoisomerase I Protein from *Staphylococcus aureus*

The polynucleotide having the DNA sequence given in (SEQ ID NO:1) was obtained from a library of clones of chromosomal DNA of *Staphylococcus aureus* in *E. coli*. In some cases the sequencing data from two or more clones containing overlapping *Staphylococcus aureus* DNA was used to construct the contiguous DNA sequence in (SEQ ID NO:1). Libraries may be prepared Libraries may be prepared by routine methods, for example, Methods 1 and 2 below.

Total cellular DNA is isolated from *Staphylococcus aureus* strain WCUH 29 according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and *E. coli* infected with the packaged library. The library is amplified by standard procedures.

Method 2

Total cellular DNA is partially hydrolysed with a combination of four restriction enzymes (RsaI, PalI, AluI and Bsh1235I) and size-fractionated according to standard procedures. EcoRI linkers are ligated to the DNA and the fragments then ligated into the vector Lambda ZapII that have been cut with EcoRI, the library packaged by standard procedures, and *E. coli* infected with the packaged library. The library is amplified by standard procedures.

Example 2

Characterization of Topoisomerase I Gene Expression a) Isolation of *Staphylococcus aureus* WCU129 RNA from infected tissue samples Infected tissue samples, in 2-ml cyro-storage tubes, are removed from −80° C. storage into a dry ice ethanol bath. In a microbiological safety cabinet the samples are disrupted up to eight at a time while the remaining samples are kept frozen in the dry ice ethanol bath. To disrupt the bacteria within the tissue sample, 50–100 mg of the tissue is transfered to a FastRNA tube containing a silica/ceramic matrix (BIO101). Immediately, 1 ml of extraction reagents (FastRNA reagents, BIO101) are added to give a sample to reagent volume ratio of approximately 1 to 20. The tubes are shaken in a reciprocating shaker (FastPrep FP120, BIO101) at 6000 rpm for 20–120 sec. The crude RNA preparation is extracted with chloroform/isoamyl alcohol, and precipitated with DEPC-treated/Isopropanol Precipitation Solution (BIO101). RNA preparations are stored in this isopropanol solution at −80° C. if necessary. The RNA is pelleted (12,000 g for 10 min.), washed with 75% ethanol (v/v in DEPC-treated water), air-dried for 5–10 min, and resuspended in 0.1 ml of DEPC-treated water.

Quality of the RNA isolated is assessed by running samples on 1% agarose gels. 1×TBE gels stained with ethidium bromide are used to visualise total RNA yields. To demonstrate the isolation of bacterial RNA from the infected tissue 1×MOPS, 2.2M formaldehyde gels are run and vacuum blotted to Hybond-N (Amersham). The blot is then hybridized with a 32 P labelled oligonucletide probe specific to 16S rRNA of *Staphylococcus aureus* (K. Greisen, M. Loeffelholz, A. Purohit and D. Leong. J. Clin. (1994) Microbiol. 32 335–351). An oligonucleotide of the sequence: 5'-gctcctaaaaggttactccaccggc-3' is used as a probe. The size of the hybridizing band is compared to that of control RNA isolated from in vitro grown *Staphylococcus aureus* WCUH29 in the Northern blot. Correct sized bacterial 16S rRNA bands can be detected in total RNA samples which show extensive degradation of the mammalian RNA when visualised on TBE gels.

b) The removal of DNA from *Staphylococcus aureus* WCUH29-derived RNA

DNA was removed from 50 microgram samples of RNA by a 30 minute treatment at 37° C. with 10 units of RNAase-free DNAaseI (GeneHunter) in the buffer supplied in a final volume of 57 microliters.

The DNAase was inactivated and removed by phenol:chloroform extraction. RNA was precipitated with 5 microliters of 3M NaOAc and 200 microliters 100% EtOH, and pelleted by centrifugation at 12,000 g for 10 minutes. The RNA is pelleted (12,000 g for 10 min.), washed with 75% ethanol (v/v in DEPC-treated water), air-dried for 5–10 min, and resuspended in 10–20 microliters of DEPC-treated water. RNA yield is quantitated by $OD_{260}$ after 1:1000 dilution of the cleaned RNA sample. RNA is stored at −80° C. if necessary and reverse-transcribed within one week.

c) The preparation of cDNA from RNA samples derived from infected tissue 10 microliter samples of DNAase treated RNA are reverse transcribed using a SuperScript Preamplification System for First Strand cDNA Synthesis kit (Gibco BRL, Life Technologies) according to the manufacturers instructions. 1 nanogram of random hexamers is used to prime each reaction. Controls without the addition of SuperScriptII reverse transcriptase are also run. Both ±RT samples are treated with RNaseH before proceeding to the PCR reaction d) The use of PCR and fluorogenic probes to determine the presence of a bacterial cDNA species Specific sequence detection occurs by amplification of target sequences in the PE Applied Biosystems 7700 Sequence Detection System in the presence of an oligonucleotide probe labeled at the 5' and 3' ends with a reporter and quencher fluorescent dye, respectively (FQ probe), which anneals between the two PCR primers. Only specific product will be detected when the probe is bound between the primers. As PCR amplification proceeds, the 5'-nuclease activity of Taq polymerase initially cleaves the reporter dye from the probe. The signal generated when the reporter dye is physically separated from the quencher dye is detected by measuring the signal with an attached CCD camera. Each signal generated equals one probe cleaved which corresponds to amplification of one target strand PCR reactions are set up using the PE Applied Biosystem TaqMan PCR Core Reagent Kit according to the instructions supplied such that each reaction contains 5 microliters 10× PCR Buffer II, 7 microliters 25 mM $MgCl_2$, 5 microliters 300 nM forward primer, 5 microliters reverse primer, 5 microliters specific FQ probe, 1 microliter each 10 mM dATP, 10 mM dCTP, 10 mM dGTP and 20 mM dUTP, 13.25 microliters distilled water, 0.5 microliters AmpErase UNG, and 0.25 microliters AmpliTaq DNA polymerase to give a total volume of 45 microliters.

Amplification proceeds under the following thermal cycling conditions:50° C. hold for 2 minutes, 95° C. hold for 10 minutes, 40 cycles of 95° C. for 15 seconds and 60° C. for 1 minute, followed by a 25° C. hold until sample is retrieved. Detection occurs real-time. Data is collected at the end of the reaction.

RT/PCR controls may include ± reverse transcriptase reactions, amplification along side genes known to be transcribed under the conditions of study and amplification of 1 microgram of genomic DNA.

Primer pairs and corresponding probes which fail to generate signal in DNA PCR or RT/PCR are PCR failures and as such are uninformative. Of those which generate signal with DNA PCR, two classes are distinguished in RT/PCR:1. Genes which are not transcribed in vivo reproducibly fail to generate signal in RT/PCR; and 2. Genes which are transcribed in vivo reproducibly generate signal in RT/PCR and show a stronger signal in the +RT samples than the signal (if at all present) in −RT controls. Based on these analyses it was discovered that *S. aureus* topoisomerase I gene was expressed in vivo.

Primers used for Example 2 are as follows:

topA fwd primer ACGAAATAACTAAAGACGCT [SEQ ID NO:5]

topA rev primer GCGAGATGTTATAGCCAACCA [SEQ ID NO:6]

topA probe FAM-ACTTAGTCGATGCACAACAAGCGCGT-TAMRA [SEQ ID NO:7]

FAM and TAMRA labeling of primers and the uses of such primer have reportsed (Lee, LG, Connell, CR, and Bloch, W. 1993. Allelic discrimination by nick-translation PCR with fluorogenic probes. Nucleic Acids Research 21:3761–3766; Livak, K. J., Flood, S. J. A., Marmaro, J., Giusti, W., and Deetz, K. 1995. Oligonucleotides with fluorescent dyes at opposite ends provide a quenched probe system useful for detecting PCR product and nucleic acid hybridization. PCR Methods and Applications 4:357–362.).

Example 3

Characterization of Topoisomerase I

The polynucleotide encoding *S. aureus* topoisomerase I was cloned into the expression vector pET28a(+) using standard techniques, to be in frame with and downstream of a 20 amino acid open reading frame, which includes 6 consecutive Histidine residues and a thrombin recognition site. The polynucleotide and polypeptide of the resulting open reading frame are below (SEQ ID NO:8 and 9):

```
ATGGGCAGCAGCCATCATCATCATCATCACAGCAGCGGCCTGGTGCCGCGCGGCAGCcat          [SEQ ID NO:8]
ATGACcTTGGCAGATAATTTAGTCATTGTTGAATCGCCTGCAAAAGCAAAAACCATTGAA
AAGTATTTAGGTAAGAAATATAAAGTTATAGCTTCAATGGGACACGTCAGAGACTTACCA
AGAAGTCAAATGGGTGTCGACACTGAAGATAATTACGAACCAAAATATATAACAATACGC
GGAAAAGGTCCTGTTGTAAAAGAATTGAAAAAACATGCAAAAAAAGCGAAAAACGTCTTT
CTCGCAAGTGACCCCGACCGTGAAGGTGAAGCAATTGCTTGGCATTTATCAAAAATTTTA
GAGCTTGAAGATTCTAAAGAAAATCGCGTTGTTTTCAACGAAATAACTAAAGACGCTGTT
AAAGAAAGTTTTAAAAATCCTAGAGAAATTGAAATGAACTTAGTCGATGCACAACAAGCG
CGTCGAATATTAGATAGATTGGTTGGCTATAACATCTCGCCAGTTCTATGGAAAAAAGTG
AAAAAAGGTTTGTCAGCGGGTCGAGTTCAATCTGTTGCACTTCGTTTAGTCATTGACCGT
GAAAATGAAATTCGAAACTTTAAACCAGAAGAATATTGGACTATTGAAGGAGAATTTAGA
TACAAAAAATCAAAATTCAATGCTAAATTCCTTCATTATAAAAATAAACCTTTTAAATTA
AAAACGAAAAAGATGTTGAGAAAATTACAGCTGCACTAGATGGAGATCAATTCGAAATT
ACAAACGTGACTAAAAAAGAAAAAACGCGTAATCCAGCAAACCCATTTACAACTTCTACA
TTACAACAAGAGGCGGCACGTAAATTAAACTTTAAAGCAAGAAAAACAATGATGGTCGCA
CAACAATTATATGAAGGTATAGATTTGAAAAAACAAGGTACGATTGGTTTAATAACATAT
ATGAGAACCGATTCTACACGTATTTCAGATACTGCCAAAGCTGAAGCAAAACAGTATATA
ACTGATAAATACGGTGAATCTTACACTTCTAAACGTAAAGCATCAGGGAAACAAGGTGAC
CAAGATGCCCATGAGGCTATTAGACCTTCAAGTACTATGCGTACGCCAGATGATATGAAG
TCATTTTTGACGAAAGACCAATACCGATTATACAAATTAATTTGGGAACGATTTGTTGCT
AGTCAAATGGCTCCAGCAATACTTGATACAGTCTCATTAGACATAACACAAGGTGACATT
AAATTTAGAGCGAATGGTCAAACAATCAAGTTTAAAGGATTTATGACACTTTATGTAGAA
ACTAAAGATGATAGTGATAGCGAAAAGGAAATAAACTGCCTAAATTAGAGCAAGGTGAT
AAAGTCACAGCAACTCAAATTGAACCAGCTCAACACTATACACAACCACCTCCAAGATAT
ACTGAGGCGAGATTAGTAAAAACACTAGAAGAATTGAAAATTGGGCGACCATCAACTTAT
GCACCGACAATAGATACGATTCAAAAGCGTAACTATGTCAAATTAGAAAGTAAGCGTTTT
GTTCCTACTGAGTTGGGAGAAATAGTTCATGAACAAGTGAAAGAATACTTCCCAGAGATT
ATTGATGTGgaaTTCACAGTGAATATGGAAACGTTACTTGATAAGATTGCAGAAGGCGAC
ATTACATGGAGAAAAGTAATAGACGGTTTCTTTAGTAGCTTTAAACAAGATGTTGAACGT
GCTGAAGAAGAGATGGAAAAGATTGAAATCAAAGATGAGCCAGCCGGTGAAGACTGTGAA
GTTTGTGGTTCTCCTATGGTTATAAAAATGGGACGCTATGGTAAGTTCATGGCTTGCTCA
AACTTCCCGGATTGTCGTAATACAAAAGCGATAGTTAAGTCTATTGGTGTTAAATGTCCA
AAATGTAATGATGGTGACGTCGTAGAAAGAAAATCTAAAAAGAATCGTGTCTTTTATGGA
TGTTCGAAATATCCTGAATGCGACTTTATCTCTTGGGATAAGCCGATTGGAAGAGATTGT
CCAAAATGTAACCAATATCTTGTTGAAAATAAAAAAGGCAAGACAACACAAGTAATATGT
TCAAATTGCGATTATAAAGAGGCAGCGCAGAAATAA
MGSSHHHHHHSSGLVPRGSHMTLADNLVIVESPAKAKTIEKYLGKKYKVIASMGHVRDLP        [SEQ ID NO:9]
RSQMGVDTEDNYEPKYITIRGKGPVVKELKKHAKKAKNVFLASDPDREGEAIAWHLSKIL
ELEDSKENRVVFNEITKDAVKESFKNPREIEMNLVDAQQARRILDRLVGYNISPVLWKKV
KKGLSAGRVQSVALRLVIDRENEIRNFKPEEYWTIEGEFRYKKSKFNAKFLHYKNKPFKL
```

-continued

```
KTKKDVEKITAALDGDQFEITNVTKKEKTRNPANPFTTSTLQQEAARKLNFKARKTMMVA

QQLYEGIDLKKQGTIGLITYMRTDSTRISDTAKAEAKQYITDKYGESYTSKRKASGKQGD

QDAHEAIRPSSTMRTPDDMKSFLTKDQYRLYKLIWERFVASQMAPAILDTVSLDITQGDI

KFRANGQTIKFKGFMTLYVETKDDSDSEKENKLPKLEQGDKVTATQIEPAQHYTQPPPRY

TEARLVKTLEELKIGRPSTYAPTIDTIQKRNYVKLESKRFVPTELGEIVHEQVKEYFPEI

IDVEFTVNMETLLDKIAEGDITWRKVIDGFFSSFKQDVERAEEEMEKIEIKDEPAGEDCE

VCGSPMVIKMGRYGKFMACSNFPDCRNTKAIVKSIGVKCPKCNDGDVVERKSKKNRVFYG

CSKYPECDFISWDKPIGRDCPKCNQYLVENKKGKTTQVICSNCDYKEAAQK
```

The expression plasmid (pET-topoI) was transformed into E. coli K12 strain LW29(DE3):pRI952 for expression. The plasmid pRI952 contains the argU and ileX genes which encode tRNAs that read AGG/AGA and AUA codons, respectively. These codons are rare in E. coli relative to S. aureus and the overexpression of their cognate tRNAs has been found to improve the translation efficiency of certain S. aureus genes, such as topoisomerase I.

For expression of the polypeptide from pET-topoI, the LW29(DE3):pRI952/pET-topoI cell line was grown in 1 liter of LB containing 1% glucose +50 ug/ml kanamycin at 37° C./250 rpm until the OD at 600 nm reached 1.0 and then expression was induced by addition of IPTG to 1 mM and continued growth at 37° C./250 rpm for 3 hours. The cells were lysed by sonication and the hexa-histidine tagged topoisomerase I was purified from the soluble fraction on a nickel-NTA column (Qiagen) according to the manufacturer's instructions. Approximately 14 mg of hexa-histidine tagged topoisomerase I was eluted in buffer containing 250 mM imidazole, at a concentration of 1.3 mg/ml and a purity of close to 90%.

The first 17 amino acids (MGSSHHHHHHSSGLVPR [SEQ ID NO:10] were specifically cleaved off using biotinylated thrombin (Novagen), which was subsequently removed by streptavidin agarose chromatography, according to the manufacturer's instructions.

The activity of Staph aureus topoisomerase I, with or without the hexa-histidine tag, was measured by a super-coiled DNA relaxation assay, in a 30 ul reaction containing HEPES 40 mM pH 8.0, magnesium acetate 2 mM, bovine serum albumin 0.1 mg/ml, glycerol 15%, topoisomerase I (0.1–6 ug) and 0.5 ug of supercoiled pBR322 substrate. Reactions were incubated for 30 minutes at 37° C. Reactions were stopped by addition of either SDS to 1% or EDTA to 50 mM and 5 ul of agarose gel loading buffer added. The samples were then electrophoresed in 0.8% agarose in 0.5×TBE buffer. After electrophoresis the gels were stained with ethidium bromide at 0.5 ug/ml and the DNA bands visualised on a UV transilluminator. Some reactions also contained potassium L-glutamate at, for example, 0.33M which stimulated relaxation activity. Staph aureus topoisomerase I, with or without the hexa-histidine, was demonstrated to relax negatively supercoiled DNA.

What is claimed is:

1. An isolated protein comprising a polypeptide, wherein the polypeptide comprises an amino acid sequence which is identical to SEQ ID NO:2 except that, over the entire length corresponding to SEQ ID NO:2, there are five to ten point mutations, wherein each point mutation is the substitution, deletion or insertion of one amino acid.

2. An isolated protein comprising a polypeptide, wherein the polypeptide comprises a amino acid sequence which is identical to SEQ ID NO:2 except that, over the entire length corresponding to SEQ ID NO:2, there are one to five point mutations, wherein each point mutation is the substitution, deletion or insertion of one amino acid.

3. The isolated protein of claim 2 wherein the amino acid sequence is identical to SEQ ID NO:2 except that, over the entire length corresponding to SEQ ID NO:2, there is one point mutation, wherein the point mutation is the substitution, deletion or insertion of one amino acid.

4. An isolated protein comprising the amino acid sequence set forth in SEQ ID NO:2.

5. A composition comprising the isolated protein of claim 4 and a pharmaceutically acceptable carrier.

6. An isolated fusion protein comprising a heterologous amino acid sequence used to the amino acid sequence set forth in SEQ ID NO:2.

7. A composition comprising the isolated fusion protein of claim 6 and a pharmaceutically acceptable carrier.

8. The isolated protein of claim 7, wherein the isolated protein consists of the amino acid sequence set forth in SEQ D NO:2.

9. A composition comprising the isolated protein of claim 8 and a pharmaceutically acceptable carrier.

10. An isolated protein comprising at least 50 consecutive amino acids of SEQ ID NO:2.

11. A composition comprising the isolated protein of claim 10 and a pharmaceutically acceptable carrier.

12. An isolated fusion protein comprising a heterologous amino acid sequence fused to the isolated protein of claim 10.

13. A composition comprising the isolated fusion protein of claim 12 and a pharmaceutically acceptable carrier.

14. An isolated protein comprising at least 3 consecutive amino acids of SEQ ID NO:2.

15. A composition comprising the isolated protein of claim 14 and a pharmaceutically acceptable carrier.

16. An isolated fission protein comprising a heterologous amino acid sequence fused to the isolated protein of claim 14.

17. A composition comprising the isolated fusion protein of claim 16 and a pharmaceutically acceptable carrier.

* * * * *